US012754656B2

(12) United States Patent
Fukuhara et al.

(10) Patent No.: US 12,754,656 B2
(45) Date of Patent: Oct. 6, 2026

(54) PATIENT INFORMATION PROCESSING METHOD, PATIENT INFORMATION PROCESSING DEVICE, AND PATIENT INFORMATION PROCESSING SYSTEM

(71) Applicant: NIHON KOHDEN CORPORATION, Tokyo (JP)

(72) Inventors: Itaru Fukuhara, Tokorozawa (JP); Mitsuhiro Oura, Tokorozawa (JP); Syuhei Kawamura, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 269 days.

(21) Appl. No.: 18/582,236

(22) Filed: Feb. 20, 2024

(65) Prior Publication Data

US 2024/0288993 A1 Aug. 29, 2024

(30) Foreign Application Priority Data

Feb. 27, 2023 (JP) ................................ 2023-028464

(51) Int. Cl.
*G06F 3/0482* (2013.01)
*G16H 10/60* (2018.01)

(52) U.S. Cl.
CPC ........... *G06F 3/0482* (2013.01); *G16H 10/60* (2018.01)

(58) Field of Classification Search
CPC ...... G06F 3/0482; G16H 10/60; G16H 20/40; G16H 40/63
See application file for complete search history.

(56) References Cited

U.S. PATENT DOCUMENTS

2008/0065422 A1* 3/2008 Weber .................... G16H 10/60 705/3
2013/0096942 A1 4/2013 Bowles et al.
2016/0253460 A1 9/2016 Kanada
2017/0228502 A1* 8/2017 Rickard ................ G16H 10/60
(Continued)

FOREIGN PATENT DOCUMENTS

JP 2003-331056 A 11/2003
JP 2015-501027 A 1/2015
(Continued)

OTHER PUBLICATIONS

Communication issued on Jun. 2, 2026 by the Japan Patent Office in Japanese Patent Application No. 2023-028464.

*Primary Examiner* — Cao H Nguyen
(74) *Attorney, Agent, or Firm* — Sughrue Mion, PLLC

(57) ABSTRACT

A patient information processing method is executed by one or more processors, and the method includes obtaining a plurality of pieces of patient information each of which is associated with respective one of a plurality of patients, and determining a display order of the pieces of patient information to be displayed on a patient information list screen based on first information and second information different from the first information. The determining the display order includes determining the display order of the pieces of patient information based on the first information such that the pieces of patient information to be displayed on the patient information list screen are displayed early according to a value of the first information, and determining a display order of patient information of patients having the same value of the first information based on the second information.

17 Claims, 28 Drawing Sheets

(56) References Cited

U.S. PATENT DOCUMENTS

| | | | | |
|---|---|---|---|---|
| 2017/0242973 | A1* | 8/2017 | Levin | G16H 10/60 |
| 2021/0290060 | A1* | 9/2021 | Ahmed | A61B 5/0816 |

FOREIGN PATENT DOCUMENTS

| | | | |
|---|---|---|---|
| JP | 2015-95217 | A | 5/2015 |
| JP | 2019-57159 | A | 4/2019 |
| JP | 2019-170851 | A | 10/2019 |
| JP | 2021-174332 | A | 11/2021 |
| WO | 2019/155825 | A1 | 8/2019 |

* cited by examiner

FIG. 4

41

PATIENT INFORMATION TABLE

| PATIENT NAME | BED LOCATION | AGE | GENDER | News SCORE | RR | SpO2 | BODY TEMPER-ATURE | Sys | HR | OXYGEN ADMINIS-TRATION | CONSCIOUS-NESS | DEVICE | NUMBER OF DAYS IN HOSPITAL |
|---|---|---|---|---|---|---|---|---|---|---|---|---|---|
| A | 3F | 11 | m | 11 | 10 | 98 | 35.9 | 78 | 35 | | V | ECMO | 14 |
| B | 4F | 43 | m | 5 | 32 | 94 | 36.7 | 125 | 44 | | | | 52 |
| C | 3F | 37 | f | 5 | 15 | 92 | 34.9 | 173 | 63 | | | ECMO | 66 |
| D | 2F | 78 | f | 3 | 15 | 98 | 35.9 | 154 | 65 | Y | | | 2 |
| E | 4F | 33 | f | 6 | 10 | 94 | 36.7 | 152 | 44 | | V | ECMO | 68 |
| F | 3F | 79 | m | 6 | 24 | 98 | 35.9 | 153 | 35 | | | | 3 |
| G | 2F | 85 | m | 4 | 7 | 98 | 35.9 | 166 | 78 | | | | 6 |
| H | 4F | 57 | f | 2 | 15 | 98 | 36.7 | 132 | 63 | Y | | | 85 |
| I | 3F | 46 | m | 9 | 6 | 92 | 35.9 | 95 | 44 | | | ECMO | 4 |
| J | 2F | 66 | m | 11 | 10 | 94 | 34.9 | 88 | 65 | | | | 3 |
| K | 3F | 89 | m | 6 | 17 | 98 | 35.9 | 152 | 63 | Y | V | | 68 |
| L | 3F | 33 | m | 5 | 22 | 92 | 36.7 | 162 | 44 | | | | 43 |

(CONT.)

(FIG. 4 CONTINUED)

| | | | | | | | | | | | | | |
|---|---|---|---|---|---|---|---|---|---|---|---|---|---|
| M | 4F | 54 | f | 4 | 10 | 98 | 34.9 | 156 | 63 | | | | 32 |
| N | 2F | 35 | f | 9 | 33 | 98 | 35.9 | 99 | 35 | | | | 32 |
| O | 4F | 75 | m | 4 | 14 | 94 | 36.7 | 152 | 75 | Y | V | | 65 |
| P | 3F | 32 | m | 6 | 11 | 92 | 39.3 | 144 | 44 | | | | 84 |
| Q | 3F | 33 | f | 5 | 10 | 98 | 35.9 | 133 | 35 | | | RESPIRATOR | 21 |
| R | 4F | 25 | f | 6 | 28 | 98 | 36.7 | 144 | 54 | | V | ECMO | 5 |
| S | 2F | 63 | m | 12 | 8 | 98 | 34.9 | 79 | 44 | Y | | | 2 |
| T | 4F | 68 | m | 6 | 10 | 94 | 35.9 | 176 | 35 | | | | 6 |
| U | 3F | 46 | m | 5 | 22 | 98 | 36.7 | 177 | 74 | | V | | 3 |
| V | 3F | 64 | f | 5 | 11 | 94 | 35.9 | 152 | 44 | Y | | | 5 |
| W | 3F | 66 | m | 5 | 10 | 98 | 35.9 | 144 | 35 | | | | 5 |
| X | 2F | 78 | f | 9 | 22 | 92 | 36.7 | 92 | 44 | Y | | | 2 |
| Y | 4F | 43 | f | 5 | 10 | 98 | 35.9 | 113 | 66 | | V | ECMO | 8 |
| Z | 2F | 44 | m | 5 | 13 | 92 | 36.7 | 117 | 35 | Y | | | 3 |

FIG. 5

DIAGRAM ILLUSTRATING EXAMPLE OF METHOD OF CALCULATING NEWS SCORE

| EVALUATION ITEM (PARAMETER) / SCORE | 3 | 2 | 1 | 0 | 1 | 2 | 3 |
|---|---|---|---|---|---|---|---|
| RESPIRATION RATE | ≤ 8 BREATHS/min | | 9 TO 11 BREATHS/min | 12 TO 20 BREATHS/min | | 21 TO 24 BREATHS/min | ≥ 25 BREATHS/min |
| $SpO_2$ | ≤ 91 | 92～93 | 94～95 | ≥ 96 | | | |
| OXYGEN SUPPORT | | YES | | NO | | | |
| BODY TEMPERATURE | ≤ 35.0°C | | 35.1～36.0°C | 36.1～38.0°C | 38.1～39.0°C | ≥ 39.1°C | |
| SYSTOLIC BLOOD PRESSURE | ≤ 90mmHg | 91～100mmHg | 101～110mmHg | 111～219mmHg | | | ≥ 220mmHg |
| HEART RATE | ≤ 40 BEATS/min | | 41 TO 50 BEATS/min | 51 TO 90 BEATS/min | 91 TO 110 BEATS/min | 111 TO 130 BEATS/min | ≥ 131 BEATS/min |
| CONSCIOUSNESS LEVEL | | | | CONSCIOUS | | | UNCONSCIOUS |

FIG. 6

42

MEDICAL WORKER INFORMATION TABLE

| NAME | DEPARTMENT | JOB TYPE | YEARS OF EXPERIENCE |
|---|---|---|---|
| AA | CARDIOVASCULAR MEDICINE | DOCTOR | 15 |
| BB | RESPIRATORY MEDICINE | DOCTOR | 6 |
| CC | CARDIAC SURGERY | DOCTOR | 17 |
| DD | CARDIOVASCULAR MEDICINE | NURSE | 22 |
| EE | RESPIRATORY MEDICINE | NURSE | 3 |
| FF | CARDIAC SURGERY | NURSE | 14 |
| GG | CARDIOVASCULAR MEDICINE | DOCTOR | 3 |

FIG. 7

43 PINNING OPERATION HISTORY TABLE

| MEDICAL WORKER | PATIENT |
|---|---|
| AA | J |
| AA | C |
| AA | W |
| GG | L |
| GG | Q |
| GG | U |
| DD | C |
| DD | Z |
| FF | Y |

*FIG. 8*

44

PATIENT COMMENT TABLE

| MEDICAL WORKER | PATIENT | COMMENT | NUMBER OF CHARACTERS OF COMMENT |
|---|---|---|---|
| AA | J | MEMO | 100 |
| AA | C | MEMO | 150 |
| AA | W | MEMO | 300 |
| GG | L | MEMO | 120 |
| GG | Q | MEMO | 110 |
| GG | U | MEMO | 60 |
| DD | C | MEMO | 80 |
| DD | W | MEMO | 40 |
| FF | J | MEMO | 50 |

(CONT.)

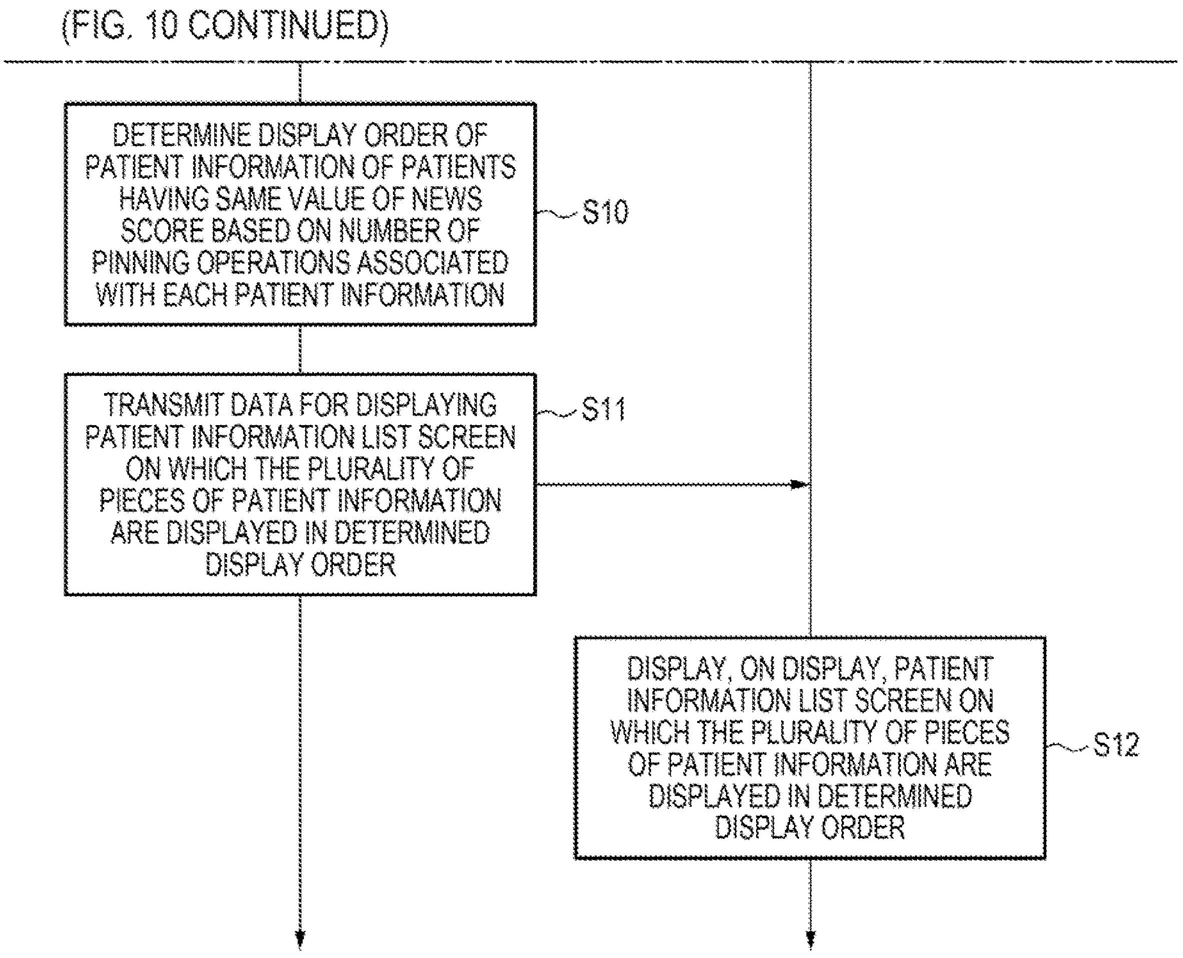
(FIG. 10 CONTINUED)
DETERMINE DISPLAY ORDER OF PATIENT INFORMATION OF PATIENTS HAVING SAME VALUE OF NEWS SCORE BASED ON NUMBER OF PINNING OPERATIONS ASSOCIATED WITH EACH PATIENT INFORMATION
S10
TRANSMIT DATA FOR DISPLAYING PATIENT INFORMATION LIST SCREEN ON WHICH THE PLURALITY OF PIECES OF PATIENT INFORMATION ARE DISPLAYED IN DETERMINED DISPLAY ORDER
S11
DISPLAY, ON DISPLAY, PATIENT INFORMATION LIST SCREEN ON WHICH THE PLURALITY OF PIECES OF PATIENT INFORMATION ARE DISPLAYED IN DETERMINED DISPLAY ORDER
S12

FIG. 11

INITIAL SCREEN OF PATIENT INFORMATION LIST SCREEN FOR MEDICAL WORKER AA

L1

| 📌 | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | A | 3F | 11 | m | 11 | 10 | 98 | 35.9 | 78 | 35 |
| ☐ | B | 4F | 43 | m | 5 | 32 | 94 | 36.7 | 125 | 44 |
| ☐ | D | 2F | 78 | f | 3 | 15 | 98 | 35.9 | 154 | 65 |
| ☐ | E | 4F | 33 | f | 6 | 10 | 94 | 36.7 | 152 | 44 |
| ☐ | F | 3F | 79 | m | 6 | 24 | 98 | 35.9 | 153 | 35 |
| ☐ | G | 2F | 85 | m | 4 | 7 | 98 | 35.9 | 166 | 78 |
| ☐ | H | 4F | 57 | f | 2 | 15 | 98 | 36.7 | 132 | 63 |
| ☐ | I | 3F | 46 | m | 9 | 6 | 92 | 35.9 | 95 | 44 |
| ☐ | K | 3F | 89 | m | 6 | 17 | 98 | 35.9 | 152 | 63 |
| ☐ | L | 3F | 33 | m | 5 | 22 | 92 | 36.7 | 162 | 44 |

(CONT.)

(FIG. 11 CONTINUED)

| | | | | | | | | | | |
|---|---|---|---|---|---|---|---|---|---|---|
| ☐ | M | 4F | 54 | f | 4 | 10 | 98 | 34.9 | 156 | 63 |
| ☐ | N | 2F | 35 | f | 9 | 33 | 98 | 35.9 | 99 | 35 |
| ☐ | O | 4F | 75 | m | 4 | 14 | 94 | 36.7 | 152 | 75 |
| ☐ | P | 3F | 32 | m | 6 | 11 | 92 | 39.3 | 144 | 44 |
| ☐ | Q | 3F | 33 | f | 5 | 10 | 98 | 35.9 | 133 | 35 |
| ☐ | R | 4F | 25 | f | 6 | 28 | 98 | 36.7 | 144 | 54 |
| ☐ | S | 2F | 63 | m | 12 | 8 | 98 | 34.9 | 79 | 44 |
| ☐ | T | 4F | 68 | m | 6 | 10 | 94 | 35.9 | 176 | 35 |
| ☐ | U | 3F | 46 | m | 5 | 22 | 98 | 36.7 | 177 | 74 |
| ☐ | V | 3F | 64 | f | 5 | 11 | 94 | 35.9 | 152 | 44 |
| ☐ | X | 2F | 78 | f | 9 | 22 | 92 | 36.7 | 92 | 44 |
| ☐ | Y | 4F | 43 | f | 5 | 10 | 98 | 35.9 | 113 | 66 |
| ☐ | Z | 2F | 44 | m | 5 | 13 | 92 | 36.7 | 117 | 35 |

FIG. 12

PATIENT INFORMATION LIST SCREEN IN WHICH DISPLAY ORDER OF PATIENT INFORMATION IS DETERMINED ACCORDING TO NEWS SCORE (FIRST PRIORITY) AND NUMBER OF PINNING OPERATIONS (SECOND PRIORITY)

| 📌 | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | S | 2F | 63 | m | 12 | 8 | 98 | 34.9 | 79 | 44 |
| ☐ | A | 3F | 11 | m | 11 | 10 | 98 | 35.9 | 78 | 35 |
| ☐ | I | 3F | 46 | m | 9 | 6 | 92 | 35.9 | 95 | 44 |
| ☐ | N | 2F | 35 | f | 9 | 33 | 98 | 35.9 | 99 | 35 |
| ☐ | X | 2F | 78 | f | 9 | 22 | 92 | 36.7 | 92 | 44 |
| ☐ | E | 4F | 33 | f | 6 | 10 | 94 | 36.7 | 152 | 44 |
| ☐ | F | 3F | 79 | m | 6 | 24 | 98 | 35.9 | 153 | 35 |
| ☐ | K | 3F | 89 | m | 6 | 17 | 98 | 35.9 | 152 | 63 |
| ☐ | P | 3F | 32 | m | 6 | 11 | 92 | 39.3 | 144 | 44 |
| ☐ | R | 4F | 25 | f | 6 | 28 | 98 | 36.7 | 144 | 54 |

(CONT.)

(FIG. 12 CONTINUED)

R1

| | | | | | | | | | | |
|---|---|---|---|---|---|---|---|---|---|---|
| ☐ | T | 4F | 68 | m | 6 | 10 | 94 | 35.9 | 176 | 35 |
| ☐ | L | 3F | 33 | m | 5 | 22 | 92 | 36.7 | 162 | 44 |
| ☐ | Q | 3F | 33 | f | 5 | 10 | 98 | 35.9 | 133 | 35 |
| ☐ | U | 3F | 46 | m | 5 | 22 | 98 | 36.7 | 177 | 74 |
| ☐ | Z | 2F | 44 | m | 5 | 13 | 92 | 36.7 | 117 | 35 |
| ☐ | Y | 4F | 43 | f | 5 | 10 | 98 | 35.9 | 113 | 66 |
| ☐ | B | 4F | 43 | m | 5 | 32 | 94 | 36.7 | 125 | 44 |
| ☐ | V | 3F | 64 | f | 5 | 11 | 94 | 35.9 | 152 | 44 |
| ☐ | G | 2F | 85 | m | 4 | 7 | 98 | 35.9 | 166 | 78 |
| ☐ | M | 4F | 54 | f | 4 | 10 | 98 | 34.9 | 156 | 63 |
| ☐ | O | 4F | 75 | m | 4 | 14 | 94 | 36.7 | 152 | 75 |
| ☐ | D | 2F | 78 | f | 3 | 15 | 98 | 35.9 | 154 | 65 |
| ☐ | H | 4F | 57 | f | 2 | 15 | 98 | 36.7 | 132 | 63 |

FIG. 13

PATIENT INFORMATION LIST SCREEN IN WHICH DISPLAY ORDER OF PATIENT INFORMATION IS DETERMINED ACCORDING TO NEWS SCORE (FIRST PRIORITY) AND NUMBER OF CHARACTERS OF COMMENT (SECOND PRIORITY)

| 📌 | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | S | 2F | 63 | m | 12 | 8 | 98 | 34.9 | 79 | 44 |
| ☐ | A | 3F | 11 | m | 11 | 10 | 98 | 35.9 | 78 | 35 |
| ☐ | I | 3F | 46 | m | 9 | 6 | 92 | 35.9 | 95 | 44 |
| ☐ | N | 2F | 35 | f | 9 | 33 | 98 | 35.9 | 99 | 35 |
| ☐ | X | 2F | 78 | f | 9 | 22 | 92 | 36.7 | 92 | 44 |
| ☐ | F | 3F | 79 | m | 6 | 24 | 98 | 35.9 | 153 | 35 |
| ☐ | K | 3F | 89 | m | 6 | 17 | 98 | 35.9 | 152 | 63 |
| ☐ | P | 3F | 32 | m | 6 | 11 | 92 | 39.3 | 144 | 44 |
| ☐ | E | 4F | 33 | f | 6 | 10 | 94 | 36.7 | 152 | 44 |
| ☐ | T | 4F | 68 | m | 6 | 10 | 94 | 35.9 | 176 | 35 |

(CONT.)

(FIG. 13 CONTINUED)

| | | | | | | | | | | |
|---|---|---|---|---|---|---|---|---|---|---|
| □ | R | 4F | 25 | f | 6 | 28 | 98 | 36.7 | 144 | 54 |
| □ | L | 3F | 33 | m | 5 | 22 | 92 | 36.7 | 162 | 44 |
| □ | Q | 3F | 33 | f | 5 | 10 | 98 | 35.9 | 133 | 35 |
| □ | U | 3F | 46 | m | 5 | 22 | 98 | 36.7 | 177 | 74 |
| □ | B | 4F | 43 | m | 5 | 32 | 94 | 36.7 | 125 | 44 |
| □ | Y | 4F | 43 | f | 5 | 10 | 98 | 35.9 | 113 | 66 |
| □ | V | 3F | 64 | f | 5 | 11 | 94 | 35.9 | 152 | 44 |
| □ | Z | 2F | 44 | m | 5 | 13 | 92 | 36.7 | 117 | 35 |
| □ | O | 4F | 75 | m | 4 | 14 | 94 | 36.7 | 152 | 75 |
| □ | M | 4F | 54 | f | 4 | 10 | 98 | 34.9 | 156 | 63 |
| □ | G | 2F | 85 | m | 4 | 7 | 98 | 35.9 | 166 | 78 |
| □ | D | 2F | 78 | f | 3 | 15 | 98 | 35.9 | 154 | 65 |
| □ | H | 4F | 57 | f | 2 | 15 | 98 | 36.7 | 132 | 63 |

R2

FIG. 14

PATIENT INFORMATION LIST SCREEN IN WHICH DISPLAY ORDER OF PATIENT INFORMATION IS DETERMINED ACCORDING TO NEWS SCORE (FIRST PRIORITY) AND NUMBER OF DAYS IN HOSPITAL (SECOND PRIORITY)

| 📌 | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | S | 2F | 63 | m | 12 | 8 | 98 | 34.9 | 79 | 44 |
| ☐ | A | 3F | 11 | m | 11 | 10 | 98 | 35.9 | 78 | 35 |
| ☐ | N | 2F | 35 | f | 9 | 33 | 98 | 35.9 | 99 | 35 |
| ☐ | I | 3F | 46 | m | 9 | 6 | 92 | 35.9 | 95 | 44 |
| ☐ | X | 2F | 78 | f | 9 | 22 | 92 | 36.7 | 92 | 44 |
| ☐ | P | 3F | 32 | m | 6 | 11 | 92 | 39.3 | 144 | 44 |
| ☐ | K | 3F | 89 | m | 6 | 17 | 98 | 35.9 | 152 | 63 |
| ☐ | E | 4F | 33 | f | 6 | 10 | 94 | 36.7 | 152 | 44 |
| ☐ | T | 4F | 68 | m | 6 | 10 | 94 | 35.9 | 176 | 35 |
| ☐ | R | 4F | 25 | f | 6 | 28 | 98 | 36.7 | 144 | 54 |

(CONT.)

(FIG. 14 CONTINUED)

| | | | | | | | | | | |
|---|---|---|---|---|---|---|---|---|---|---|
| ☐ | F | 3F | 79 | m | 6 | 24 | 98 | 35.9 | 153 | 35 |
| ☐ | B | 4F | 43 | m | 5 | 32 | 94 | 36.7 | 125 | 44 |
| ☐ | L | 3F | 33 | m | 5 | 22 | 92 | 36.7 | 162 | 44 |
| ☐ | Q | 3F | 33 | f | 5 | 10 | 98 | 35.9 | 133 | 35 |
| ☐ | Y | 4F | 43 | f | 5 | 10 | 98 | 35.9 | 113 | 66 |
| ☐ | V | 3F | 64 | f | 5 | 11 | 94 | 35.9 | 152 | 44 |
| ☐ | U | 3F | 46 | m | 5 | 22 | 98 | 36.7 | 177 | 74 |
| ☐ | Z | 2F | 44 | m | 5 | 13 | 92 | 36.7 | 117 | 35 |
| ☐ | O | 4F | 75 | m | 4 | 14 | 94 | 36.7 | 152 | 75 |
| ☐ | M | 4F | 54 | f | 4 | 10 | 98 | 34.9 | 156 | 63 |
| ☐ | G | 2F | 85 | m | 4 | 7 | 98 | 35.9 | 166 | 78 |
| ☐ | D | 2F | 78 | f | 3 | 15 | 98 | 35.9 | 154 | 65 |
| ☐ | H | 4F | 57 | f | 2 | 15 | 98 | 36.7 | 132 | 63 |

FIG. 15

PATIENT INFORMATION LIST SCREEN IN WHICH DISPLAY ORDER OF PATIENT INFORMATION IS DETERMINED ACCORDING TO NEWS SCORE (FIRST PRIORITY) AND SPECIFIC MEDICAL DEVICE (SECOND PRIORITY)

| (pin) | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | S | 2F | 63 | m | 12 | 8 | 98 | 34.9 | 79 | 44 |
| ☐ | A | 3F | 11 | m | 11 | 10 | 98 | 35.9 | 78 | 35 |
| ☐ | I | 3F | 46 | m | 9 | 6 | 92 | 35.9 | 95 | 44 |
| ☐ | N | 2F | 35 | f | 9 | 33 | 98 | 35.9 | 99 | 35 |
| ☐ | X | 2F | 78 | f | 9 | 22 | 92 | 36.7 | 92 | 44 |
| ☐ | E | 4F | 33 | f | 6 | 10 | 94 | 36.7 | 152 | 44 |
| ☐ | R | 4F | 25 | f | 6 | 28 | 98 | 36.7 | 144 | 54 |
| ☐ | F | 3F | 79 | m | 6 | 24 | 98 | 35.9 | 153 | 35 |
| ☐ | K | 3F | 89 | m | 6 | 17 | 98 | 35.9 | 152 | 63 |
| ☐ | P | 3F | 32 | m | 6 | 11 | 92 | 39.3 | 144 | 44 |

(CONT.)

(FIG. 15 CONTINUED)

| | | | | | | | | | | |
|---|---|---|---|---|---|---|---|---|---|---|
| ☐ | T | 4F | 68 | m | 6 | 10 | 94 | 35.9 | 176 | 35 |
| ☐ | Y | 4F | 43 | f | 5 | 10 | 98 | 35.9 | 113 | 66 |
| ☐ | Q | 3F | 33 | f | 5 | 10 | 98 | 35.9 | 133 | 35 |
| ☐ | B | 4F | 43 | m | 5 | 32 | 94 | 36.7 | 125 | 44 |
| ☐ | L | 3F | 33 | m | 5 | 22 | 92 | 36.7 | 162 | 44 |
| ☐ | U | 3F | 46 | m | 5 | 22 | 98 | 36.7 | 177 | 74 |
| ☐ | V | 3F | 64 | f | 5 | 11 | 94 | 35.9 | 152 | 44 |
| ☐ | Z | 2F | 44 | m | 5 | 13 | 92 | 36.7 | 117 | 35 |
| ☐ | G | 2F | 85 | m | 4 | 7 | 98 | 35.9 | 166 | 78 |
| ☐ | M | 4F | 54 | f | 4 | 10 | 98 | 34.9 | 156 | 63 |
| ☐ | O | 4F | 75 | m | 4 | 14 | 94 | 36.7 | 152 | 75 |
| ☐ | D | 2F | 78 | f | 3 | 15 | 98 | 35.9 | 154 | 65 |
| ☐ | H | 4F | 57 | f | 2 | 15 | 98 | 36.7 | 132 | 63 |

FIG. 16

PATIENT INFORMATION LIST SCREEN IN WHICH DISPLAY ORDER OF PATIENT INFORMATION IS DETERMINED ACCORDING TO NEWS SCORE (FIRST PRIORITY), SPECIFIC MEDICAL DEVICE (SECOND PRIORITY), AND NUMBER OF DAYS IN HOSPITAL (THIRD PRIORITY)

| 📌 | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | J | 2F | 66 | m | 11 | 10 | 94 | 34.9 | 88 | 65 |
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | S | 2F | 63 | m | 12 | 8 | 98 | 34.9 | 79 | 44 |
| ☐ | A | 3F | 11 | m | 11 | 10 | 98 | 35.9 | 78 | 35 |
| ☐ | I | 3F | 46 | m | 9 | 6 | 92 | 35.9 | 95 | 44 |
| ☐ | N | 2F | 35 | f | 9 | 33 | 98 | 35.9 | 99 | 35 |
| ☐ | X | 2F | 78 | f | 9 | 22 | 92 | 36.7 | 92 | 44 |
| ☐ | E | 4F | 33 | f | 6 | 10 | 94 | 36.7 | 152 | 44 |
| ☐ | R | 4F | 25 | f | 6 | 28 | 98 | 36.7 | 144 | 54 |
| ☐ | P | 3F | 32 | m | 6 | 11 | 92 | 39.3 | 144 | 44 |
| ☐ | K | 3F | 89 | m | 6 | 17 | 98 | 35.9 | 152 | 63 |
| ☐ | T | 4F | 68 | m | 6 | 10 | 94 | 35.9 | 176 | 35 |

(CONT.)

(FIG. 16 CONTINUED)

| | | | | | | | | | | |
|---|---|---|---|---|---|---|---|---|---|---|
| ☐ | F | 3F | 79 | m | 6 | 24 | 98 | 35.9 | 153 | 35 |
| ☐ | Y | 4F | 43 | f | 5 | 10 | 98 | 35.9 | 113 | 66 |
| ☐ | Q | 3F | 33 | f | 5 | 10 | 98 | 35.9 | 133 | 35 |
| ☐ | B | 4F | 43 | m | 5 | 32 | 94 | 36.7 | 125 | 44 |
| ☐ | L | 3F | 33 | m | 5 | 22 | 92 | 36.7 | 162 | 44 |
| ☐ | V | 3F | 64 | f | 5 | 11 | 94 | 35.9 | 152 | 44 |
| ☐ | U | 3F | 46 | m | 5 | 22 | 98 | 36.7 | 177 | 74 |
| ☐ | Z | 2F | 44 | m | 5 | 13 | 92 | 36.7 | 117 | 35 |
| ☐ | O | 4F | 75 | m | 4 | 14 | 94 | 36.7 | 152 | 75 |
| ☐ | M | 4F | 54 | f | 4 | 10 | 98 | 34.9 | 156 | 63 |
| ☐ | G | 2F | 85 | m | 4 | 7 | 98 | 35.9 | 166 | 78 |
| ☐ | D | 2F | 78 | f | 3 | 15 | 98 | 35.9 | 154 | 65 |
| ☐ | H | 4F | 57 | f | 2 | 15 | 98 | 36.7 | 132 | 63 |

(FIG. 17 CONTINUED)
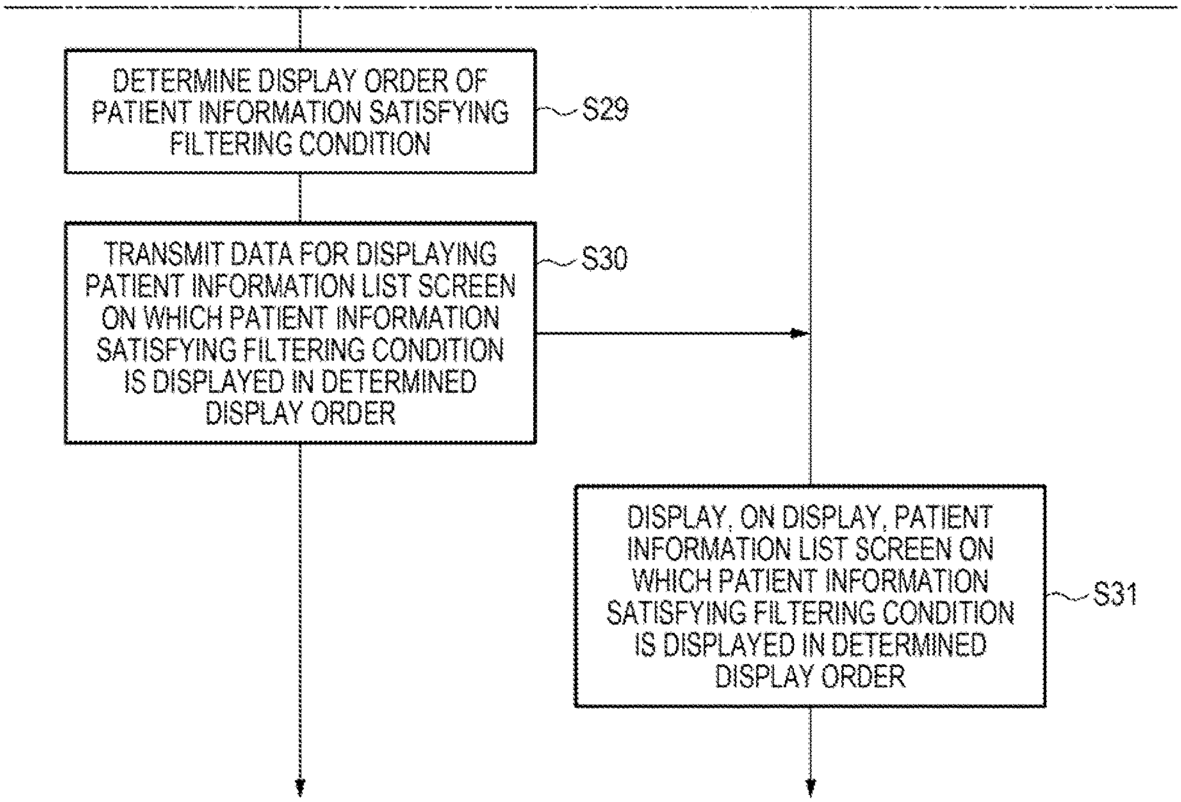

FIG. 18

PATIENT INFORMATION LIST SCREEN IN WHICH DISPLAY ORDER OF PATIENT INFORMATION SATISFYING FILTERING CONDITION IN WHICH BED LOCATION IS 3F IS DETERMINED ACCORDING TO NEWS SCORE

| | PATIENT NAME | BED LOCATION | AGE | GENDER | News SCORE | RR | SpO2 | BODY TEMPERATURE | Sys | HR |
|---|---|---|---|---|---|---|---|---|---|---|
| ☑ | C | 3F | 37 | f | 5 | 15 | 92 | 34.9 | 173 | 63 |
| ☑ | W | 3F | 66 | m | 5 | 10 | 98 | 35.9 | 144 | 35 |
| ☐ | A | 3F | 11 | m | 11 | 10 | 98 | 35.9 | 78 | 35 |
| ☐ | I | 3F | 46 | m | 9 | 6 | 92 | 35.9 | 95 | 44 |
| ☐ | F | 3F | 79 | m | 6 | 24 | 98 | 35.9 | 153 | 35 |
| ☐ | K | 3F | 89 | m | 6 | 17 | 98 | 35.9 | 152 | 63 |
| ☐ | P | 3F | 32 | m | 6 | 11 | 92 | 39.3 | 144 | 44 |
| ☐ | L | 3F | 33 | m | 5 | 22 | 92 | 36.7 | 162 | 44 |
| ☐ | Q | 3F | 33 | f | 5 | 10 | 98 | 35.9 | 133 | 35 |
| ☐ | U | 3F | 46 | m | 5 | 22 | 98 | 36.7 | 177 | 74 |
| ☐ | V | 3F | 64 | f | 5 | 11 | 94 | 35.9 | 152 | 44 |

PATIENT INFORMATION PROCESSING METHOD, PATIENT INFORMATION PROCESSING DEVICE, AND PATIENT INFORMATION PROCESSING SYSTEM

CROSS-REFERENCE TO RELATED APPLICATIONS

The present application claims the benefit of priority of Japanese Patent Application No. 2023-028464, filed on Feb. 27, 2023, the content of which is incorporated herein by reference.

TECHNICAL FIELD

The present disclosure relates to a patient information processing method, a patient information processing device, and a patient information processing system. Furthermore, the present disclosure relates to a program that causes a computer to execute the patient information processing method, and a computer readable storage medium that stores the program.

BACKGROUND ART

In the world, a pandemic due to a novel coronavirus infectious disease (COVID-19) still rages, and in a specific medical institution, the management of a severe patient has become a very important factor with an explosive increase of a patient infected with the novel coronavirus. In particular, in a medical field, a vital score (for example, National Early Warning Score (NEWS)) indicating a condition of a patient are effectively used for the management of a severe patient.

JP2019-170851A discloses a patient information device that calculates a vital score for each patient based on vital data of the patient and displays a patient information list screen including a plurality of pieces of patient information. A medical worker can grasp the condition of each patient by checking each piece of patient information displayed on the patient information list screen.

SUMMARY OF INVENTION

In the patient information list screen disclosed in JP2019-170851A, the patient information including various vital scores can be checked for each patient. On the other hand, since the patient information is not displayed on the patient information list screen according to severity (that is, a value of the vital score) of the patient, it is difficult for the medical worker to intuitively grasp the patient having a high priority (severity) through the patient information list screen. Further, even when the patient information is displayed on the patient information list screen in a descending order according to the value of the vital score, there is room for consideration in how to determine a display order of the patient information of patients having the same value of the vital score. For example, when there are ten or more severe patients having a NEWS score of 10 points, there is room for consideration in how to determine a display order of patient information of the severe patients having the NEWS score of 10 points. Further, in consideration of an attribute of the medical worker (for example, a department to which the medical worker belongs), there is room for consideration as to which patient information among a large number of patient information is displayed on the patient information list screen.

An object of the present disclosure is to provide a patient information processing method, a patient information processing device, and a patient information processing system capable of easily grasping patient information of a patient having a high priority through a patient information list screen. Further, another object of the present disclosure is to provide a program that causes a computer to execute the patient information processing method, and a computer readable storage medium that stores the program.

A patient information processing method according to an aspect of the presently disclosed subject matter is executed by one or more processors, and the method includes

- obtaining a plurality of pieces of patient information each of which is associated with respective one of a plurality of patients, and
- determining a display order of the pieces of patient information to be displayed on a patient information list screen based on first information and second information different from the first information.

The determining the display order includes

- determining the display order of the pieces of patient information based on the first information such that the pieces of patient information to be displayed on the patient information list screen are displayed early according to a value of the first information, and
- determining a display order of patient information of patients having the same value of the first information based on the second information.

According to the above method, the display order of the pieces of patient information is determined based on the first information such that the pieces of the patient information to be displayed on the patient information list screen are displayed early according to the value of the first information, and the display order of the patient information of the patients having the same value of the first information is determined based on the second information. As described above, since the display order of the pieces of patient information to be displayed on the patient information list screen is finely determined based on the two different information, that is, the first information and the second information, a medical worker can easily grasp the patient information of the patient having a high priority through the patient information list screen.

A patient information processing method according to another aspect of the presently disclosed subject matter is executed by one or more processors, and the method includes

- obtaining a plurality of pieces of patient information each of which is associated with respective one of a plurality of patients,
- determining a plurality of pieces of first patient information to be displayed on a patient information list screen by filtering the plurality of pieces of patient information based on a predetermined filtering condition, and
- determining a display order of the plurality of pieces of first patient information to be displayed on the patient information list screen based on information different from the predetermined filtering condition.

According to the above method, the plurality of pieces of first patient information to be displayed on the patient information list screen are determined by filtering the plurality of pieces of patient information based on the predetermined filtering condition, and the display order of the plurality of pieces of first patient information to be displayed on the patient information list screen is determined based on the information different from the predetermined filtering condition. As described above, since the patient information to be displayed on the patient information list screen and the display order of the patient information are determined based on the two different information, the medical worker can easily grasp the patient information having the high priority through the patient information list screen.

A program that causes a computer to execute the patient information processing method and a computer readable medium that stores the program may be provided.

A patient information processing device according to an aspect of the presently disclosed subject matter includes one or more processors, and one or more memories configured to store a computer readable instruction.

When the computer readable instruction is executed by the one or more processors, the patient information processing device obtains a plurality of pieces of patient information each of which is associated with respective one of a plurality of patients, and determines a display order of the pieces of patient information to be displayed on a patient information list screen based on first information and second information different from the first information, and when determining the display order, the patient information processing device determines the display order of the pieces of patient information based on the first information such that the pieces of patient information to be displayed on the patient information list screen are displayed early according to a value of the first information, and determines a display order of patient information of patients having the same value of the first information based on the second information.

According to the above configuration, the medical worker can easily grasp the patient information of the patient having the high priority through the patient information list screen. Thus, it is possible to provide a patient information processing device having improved usability.

A patient information processing device according to another aspect of the presently disclosed subject matter includes one or more processors, and one or more memories configured to store a computer readable instruction.

When the computer readable instruction is executed by the one or more processors, the patient information processing device obtains a plurality of pieces of patient information each of which is associated with respective one of a plurality of patients, determines a plurality of pieces of first patient information to be displayed on a patient information list screen by filtering the plurality of pieces of patient information based on a predetermined filtering condition, and determines a display order of the plurality of pieces of first patient information to be displayed on the patient information list screen based on information different from the predetermined filtering condition.

According to the above configuration, the medical worker can easily grasp the patient information of the patient having the high priority through the patient information list screen. Thus, it is possible to provide the patient information processing device having the improved usability.

A patient information processing system according to an aspect of the presently disclosed subject matter includes a server, and a display terminal communicably connected to the server.

The patient information processing system obtains a plurality of pieces of patient information each of which is associated with respective one of a plurality of patients, determines a display order of the pieces of patient information to be displayed on a patient information list screen based on first information and second information different from the first information, and displays the patient information list screen in which the plurality of pieces of patient information are displayed in the determined display order, and when determining the display order, the patient information processing system determines the display order of the pieces of patient information based on the first information such that the pieces of patient information to be displayed on the patient information list screen are displayed early according to a value of the first information, and determines a display order of patient information of patients having the same value of the first information based on the second information.

According to the above configuration, the display order of the pieces of patient information is determined based on the first information such that the pieces of the patient information to be displayed on the patient information list screen are displayed early according to the value of the first information, and the display order of the patient information of the patients having the same value of the first information is determined based on the second information. Thus, since the display order of the pieces of patient information to be displayed on the patient information list screen is finely determined based on the two different information, that is, the first information and the second information, the medical worker can easily grasp the patient information of the patient having a high priority through the displayed patient information list screen.

A patient information processing system according to another aspect of the presently disclosed subject matter includes a server, and a display terminal communicably connected to the server.

The patient information processing system obtains a plurality of pieces of patient information each of which is associated with respective one of a plurality of patients, determines a plurality of pieces of first patient information to be displayed on a patient information list screen by filtering the plurality of pieces of patient information based on a predetermined filtering condition, determines a display order of the plurality of pieces of first patient information to be displayed on the patient information list screen based on information different from the predetermined filtering condition, and displays the patient information list screen on which the plurality of pieces of first patient information are displayed in the determined display order.

According to the above configuration, the plurality of pieces of first patient information to be displayed on the patient information list screen are determined by filtering the plurality of pieces of patient information based on the predetermined filtering condition, and the display order of the plurality of pieces of first patient information to be displayed on the patient information list screen is determined based on the information different from the predetermined filtering condition. Thus, since the patient information to be displayed on the patient information list screen and the display order of the patient information are determined based on the two different information, the medical worker can easily grasp the patient information of the patient having the high priority through the displayed patient information list screen.

According to the present disclosure, it is possible to provide a patient information processing method, a patient information processing device, and a patient information processing system capable of easily grasping patient information of a patient having a high priority through a patient information list screen. Further, the present disclosure can provide a program that causes a computer to execute the patient information processing method, and a computer readable storage medium that stores the program.

BRIEF DESCRIPTION OF DRAWINGS

FIG. 4 is a diagram illustrating an example of a patient information table.

FIG. 5 is a diagram illustrating an example of a method of calculating a NEWS score.

FIG. 6 is a diagram illustrating an example of a medical worker information table.

FIG. 7 is a diagram illustrating an example of a pinning operation history table.

FIG. 8 is a diagram illustrating an example of a patient comment table.

FIG. 11 is a diagram illustrating an example of an initial screen of a patient information list screen for a medical worker AA.

FIG. 12 is a diagram illustrating an example of the patient information list screen in which a display order of patient information is determined according to a NEWS score (first priority) and the number of pinning operations (second priority).

FIG. 13 is a diagram illustrating an example of the patient information list screen in which the display order of the patient information is determined according to the NEWS score (first priority) and the number of characters of a comment (second priority).

FIG. 14 is a diagram illustrating an example of the patient information list screen in which the display order of the patient information is determined according to the NEWS score (first priority) and the number of days in a hospital (second priority).

FIG. 15 is a diagram illustrating an example of the patient information list screen in which the display order of the patient information is determined according to the NEWS score (first priority) and presence or absence of connection of a specific medical device (second priority).

FIG. 16 is a diagram illustrating an example of the patient information list screen in which the display order of the patient information is determined according to the NEWS score (first priority), the presence or absence of the connection of the specific medical device (second priority), and the number of days in a hospital (third priority).

FIG. 18 is a diagram illustrating an example of a patient information list screen in which a display order of patient information satisfying a filtering condition in which a bed location of a patient is 3F is determined according to an NEWS score.

DESCRIPTION OF EMBODIMENTS

Figure 1:
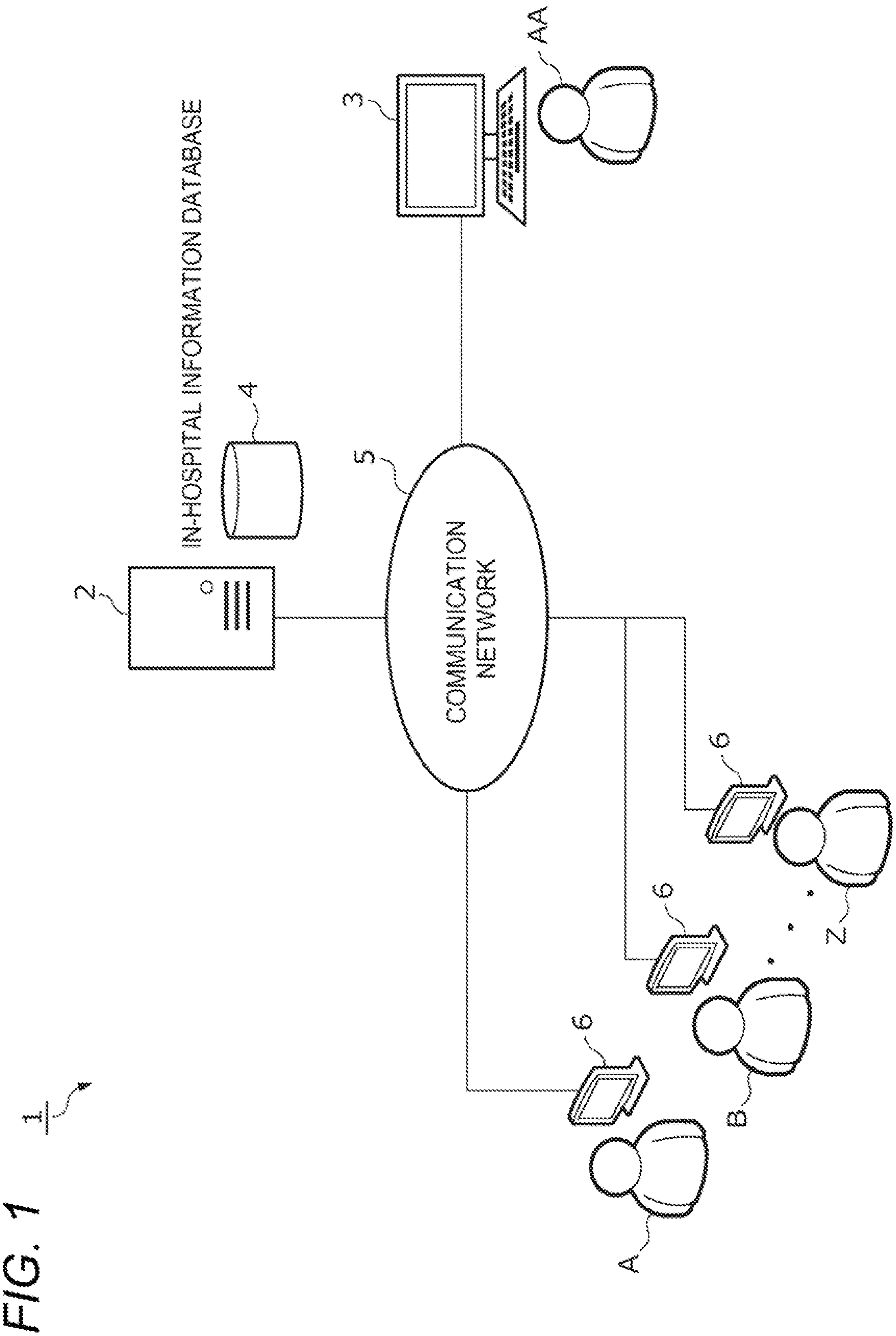
FIG. 1 is a diagram illustrating an example of a configuration of a patient information processing system according to an embodiment of the present disclosure (hereinafter, referred to as the present embodiment).

Hereinafter, the present embodiment will be described with reference to the drawings. First, a patient information processing system 1 according to the present embodiment will be described below with reference to FIG. 1. FIG. 1 is a diagram illustrating an example of a configuration of the patient information processing system 1 (hereinafter, referred to as a processing system 1) according to the present embodiment. As illustrated in FIG. 1, the processing system 1 includes a server 2, a plurality of bed-side monitors 6, and a display terminal 3. The server 2 is communicably connected to the plurality of bed-side monitors 6 and the display terminal 3 via a communication network 5.

The communication network 5 may be an in-hospital network including, for example, a local area network (LAN) or a wide area network (WAN). Further, the communication network 5 may include an in-hospital network and the Internet. In this case, the server 2 may be a server installed in the in-hospital network or an external server (for example, a cloud server) installed outside the in-hospital network.

The server 2 includes an in-hospital information database 4. The in-hospital information database 4 is built in, for example, a storage device 21 (see FIG. 2). The in-hospital information database 4 may be built in another database server communicably connected to the server 2.

Figure 2:
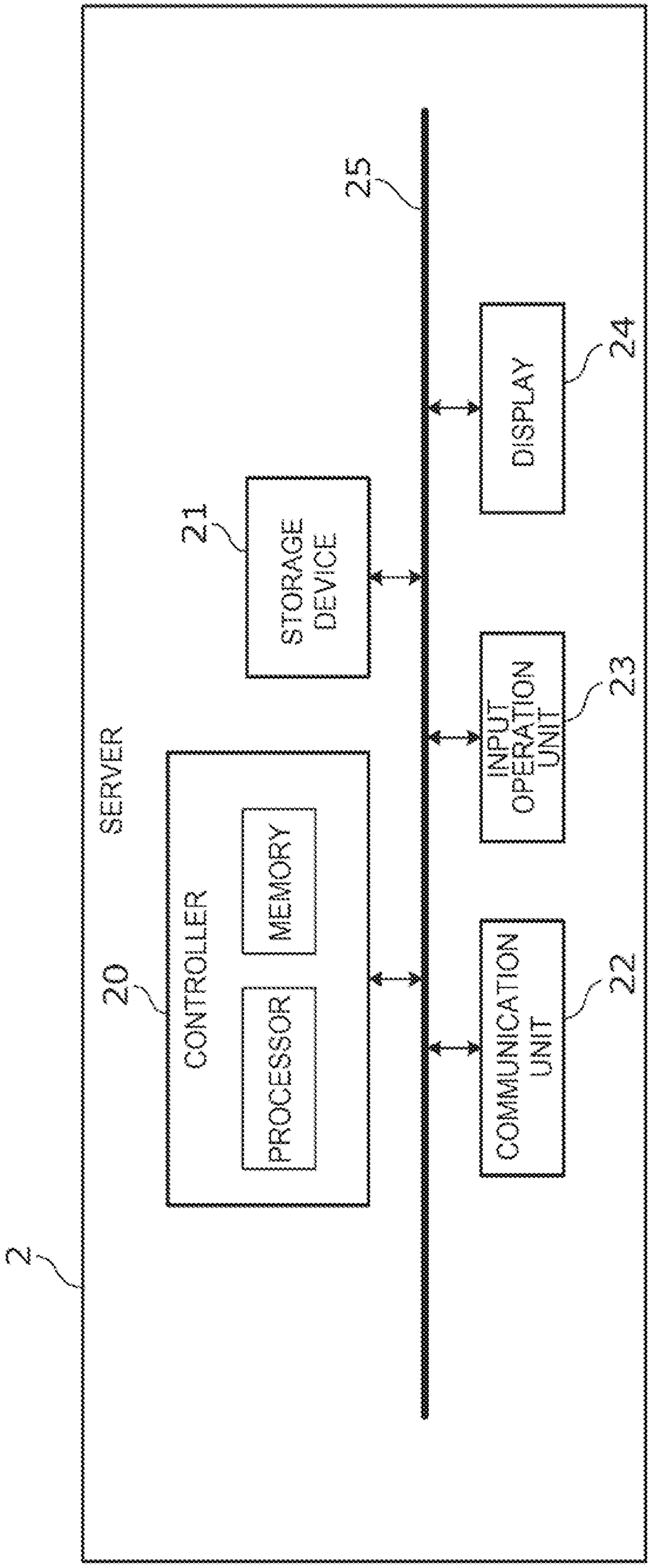
FIG. 2 is a diagram illustrating an example of a hardware configuration of a server.

Next, a hardware configuration of the server 2 will be described with reference to FIG. 2. FIG. 2 is a diagram illustrating an example of the hardware configuration of the server 2.

As illustrated in FIG. 2, the server 2 includes a controller 20, the storage device 21, a communication unit 22, an input operation unit 23, and a display 24. These components are communicably connected to one another via a bus 25.

The controller 20 includes one or more memories and one or more processors. Each memory is configured to store a computer readable instruction (program). For example, the memory may include a read only memory (ROM) in which various programs are stored, and a random access memory (RAM) having a plurality of work areas in which various programs executed by the one or more processors are stored. Each processor may include at least one of, for example, a central processing unit (CPU), a micro processing unit (MPU), and a graphics processing unit (GPU). The CPU may include a plurality of CPU cores. The GPU may include a plurality of GPU cores. The processor may be configured to load a program designated from various programs incorporated in the storage device 21 or ROM into RAM, and configured to execute various processes in cooperation with the RAM. In particular, the processor loads a patient information processing program that executes a series of processes (for example, see FIG. 10) of the server 2 into the RAM, and executes the program in cooperation with the RAM, whereby the controller 20 executes the series of processes illustrated in FIG. 10. Details of the patient information processing program will be described later.

The storage device 21 is a storage device (storage) such as a hard disk drive (HDD), a solid state drive (SSD), or a flash memory, and is configured to store programs and various data. The patient information processing program may be incorporated in the storage device 21. In addition, the in-hospital information database 4 is stored in the storage device 21.

The communication unit 22 is configured to connect the server 2 to the communication network 5. Specifically, the communication unit 22 may include various wired connection terminals for communicating with each device disposed on the communication network 5. In addition, the communication unit 22 may include a wireless communication module for wirelessly communicating with each device. The input operation unit 23 is, for example, a touch panel, a mouse, and/or a keyboard, which are overlaid and disposed over the display 24. The input operation unit 23 is configured to receive an input operation of an operator and generate an operation signal corresponding to the input operation of the operator. The display 24 includes, for example, a liquid crystal panel or an organic EL panel.

Figure 3:
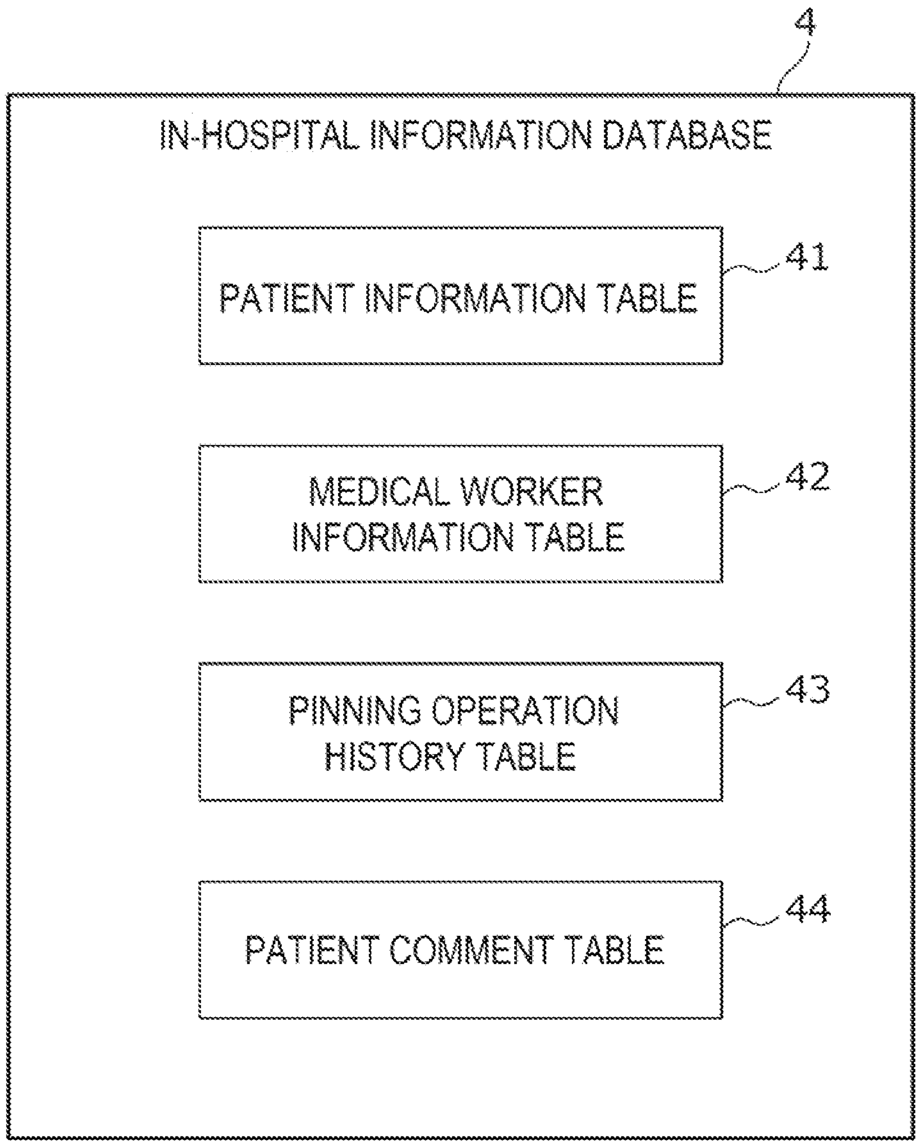
FIG. 3 is a diagram illustrating an example of various tables in an in-hospital information database.

Next, the in-hospital information database 4 built in the storage device 21 will be described with reference to FIG. 3. As illustrated in FIG. 3, the in-hospital information database 4 includes a patient information table 41, a medical worker information table 42, a pinning operation history table 43, and a patient comment table 44.

FIG. 4 is a diagram illustrating an example of the patient information table 41. As illustrated in FIG. 4, the patient information table 41 includes attribute information of a patient, information indicating vital data of the patient, information indicating an NEWS score of the patient, information indicating a medical device connected to the patient, and information indicating the number of days in a hospital of the patient. Further, the patient information table 41 further includes information indicating presence or absence of oxygen administration and information indicating presence or absence of consciousness of the patient. These information in the patient information table 41 may be updated at predetermined time intervals.

The attribute information of the patient includes information indicating a patient name, a bed location, an age, and a gender. The information indicating the vital data of the patient includes information indicating a respiration rate (RR), an oxygen saturation (SpO2), a body temperature, a systolic blood pressure (Sys), and a heart rate (HR).

In the description of the present embodiment, the NEWS score is calculated as an example of the vital score indicating a condition of the patient. For example, as illustrated in FIG. 5, the server 2 calculates the NEWS score based on each piece of vital data, the presence or absence of oxygen administration, and the presence or absence of consciousness of the patient. Specifically, the server 2 calculates a sub score of each of the plurality of pieces of vital data in accordance with a comparison between each of the plurality of pieces of vital data and a reference range set for each of the plurality of pieces of vital data. For example, when the respiration rate (RR) is 12 breaths/min to 20 breaths/min, the sub score related to the respiration rate is zero. When the respiration rate is 9 breaths/min to 11 breaths/min, the sub score related to the respiration rate is one. When the respiration rate is 21 breaths/min to 24 breaths/min, the sub score related to the respiration rate is two. When the respiration rate is 8 breaths/min or less or 25 breaths/min or more, the sub score related to the respiration rate is three. Furthermore, the server 2 calculates a sub score related to the oxygen administration and a sub score related to the consciousness of the patient. For example, when the oxygen administration is not performed, the sub score related to the oxygen administration is two. On the other hand, when the oxygen administration is not performed, the sub score related to the oxygen administration is zero. When the patient is not conscious, the sub score related to the consciousness of the patient is 3. On the other hand, when the patient is conscious, the sub score related to the consciousness of the patient is zero.

In this manner, the server 2 calculates the NEWS score of the patient by summing up the calculated sub scores. For example, as illustrated in FIG. 4, the respiration rate (RR) of a patient A is 10 breaths/min, and therefore, the sub score related to the respiration rate is one. The oxygen saturation (SpO2) of the patient A is 98%, and therefore, the sub score related to the oxygen saturation is zero. The body temperature of the patient A is 35.9° C., and therefore, the sub score related to the body temperature is one. The systolic blood pressure (Sys) of the patient A is 78 mmHg, and therefore, the sub score related to the systolic blood pressure is three. The heart rate (HR) of the patient A is 35 beats/min, and therefore, the sub score related to the heart rate is three. Since the patient A is not administered with oxygen, the sub score related to the oxygen administration is 0. The patient A is not conscious, and therefore, the sub score related to the consciousness of the patient is three. Thus, the NEWS score of the patient A is 11 (=1+1+3+3+3) by summing up the sub scores.

In the present embodiment, the vital score is not limited to the NEWS score. For example, as another example of the vital score, SOFA, qSOFA, APACHE2, BSAS, NIHSS, or the like may be adopted. Further, in the present embodiment, the respiration rate, the oxygen saturation, the body temperature, the systolic blood pressure, and the heart rate are obtained as the vital data of the patient in order to calculate the NEWS score, but a type of the vital data of the patient may be changed in accordance with a type of the vital score to be adopted.

Each piece of vital data in the patient information table 41 is updated at predetermined time intervals. As illustrated in FIG. 1, the vital data of each patient is transmitted from the plurality of bed-side monitors 6 (example of a patient monitor) to the server 2 via the communication network 5 at predetermined time intervals. Each of the plurality of bed-side monitors 6 is connected to respective one of patients A to Z. Each of the bed-side monitors 6 includes a plurality of vital sensors for measuring the vital data such as a respiration rate and a heart rate of the patient. The plurality of vital sensors may include, for example, a respiration sensor, an SpO2 sensor, a body temperature sensor, a blood pressure sensor, and an electrocardiogram sensor.

When an extracorporeal membrane oxygenation (ECMO) is connected to the patient, information indicating ECMO is input as information indicating the medical device connected to the patient. When a respirator is connected to the patient, information indicating the respirator is input as information indicating the medical device connected to the patient. The medical device connected to the patient is not limited to ECMO or the respirator, and may be a medical device such as a CO2 sensor or a pacemaker.

The information indicating the number of days in a hospital of the patient may be calculated by the server 2 based on a difference between a hospitalization date of the patient and a current date. In this manner, the information indicating the number of days in a hospital of the patient is updated every day. Each of the information indicating the presence or absence of oxygen administration, the information indicating the presence or absence of the consciousness of the patient, the information indicating the medical device connected to the patient, and the information indicating the hospitalization date of the patient may be directly input to the server 2 through the input operation unit 23 of the server 2. Alternatively, the server 2 may receive the information from an electronic medical record server (not illustrated) disposed on the communication network 5 at predetermined time intervals.

FIG. 6 is a diagram illustrating an example of the medical worker information table 42. As illustrated in FIG. 6, the medical worker information table 42 includes information (name, department to which the medical worker belongs, job type, years of experience, and the like) indicating an attribute of each medical worker.

FIG. 7 is a diagram illustrating an example of the pinning operation history table 43. As illustrated in FIG. 7, the pinning operation history table 43 includes information indicating a medical worker who has performed a pinning operation and information indicating a patient who has been pinned by the medical worker. In the pinning operation history table 43, the medical worker who has performed the pinning operation and the patient who has been pinned are associated with each other. For example, in FIG. 7, it is understood that patient information of patients J, C, and W is pinned by the medical worker AA. The server 2 may update the pinning operation history table 43 when information related to the pinning operation performed by the medical worker is received from the display terminal 3. For example, when the medical worker AA pins the patient information of the patients J, C, and W through a patient information list screen (see FIG. 11) displayed on the display terminal 3, information indicating that the patient information of the patients J, C, and W is pinned by the medical worker AA is transmitted from the display terminal 3 to the server 2 via the communication network 5. Thereafter, the server 2 updates the pinning operation history table 43 in response to the reception of the information.

FIG. 8 is a diagram illustrating an example of the patient comment table 44. As illustrated in FIG. 8, the patient comment table 44 includes information indicating a medical worker who has made a comment on a patient, information indicating the patient for whom the comment has been made, information indicating a content of the comment on the patient, and information indicating the number of characters of the comment. In the example of the patient comment table 44 illustrated in FIG. 8, it is understood that the medical worker AA inputs a comment related to a condition of the patient J, and the number of characters of the comment is 100. For example, when the medical worker AA inputs a comment on the condition of the patient J through the patient information list screen (see FIG. 11) displayed on the display terminal 3, information on the comment on the patient J input by the medical worker AA is transmitted from the display terminal 3 to the server 2 via the communication network 5. Thereafter, the server 2 updates the patient comment table 44 in response to the reception of the information.

Figure 9:
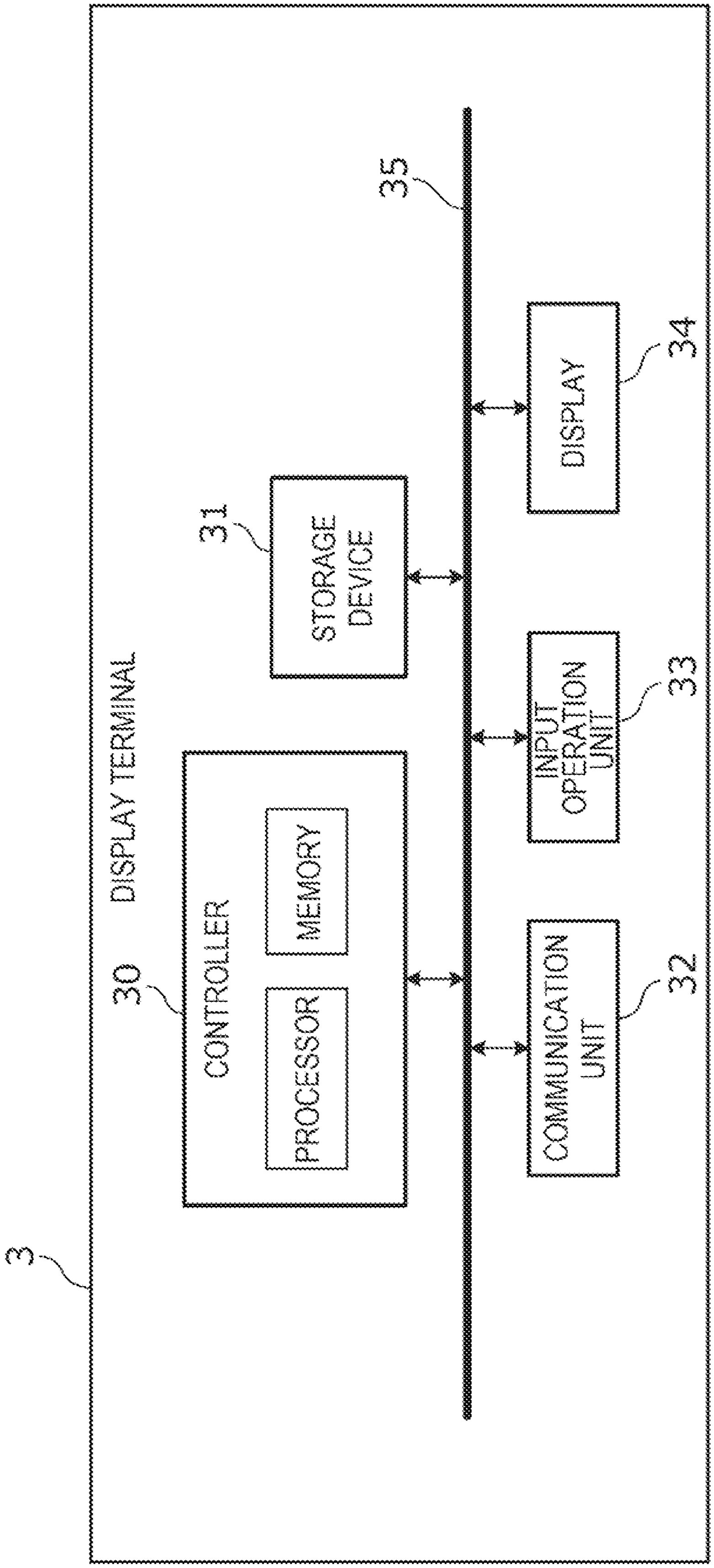
FIG. 9 is a diagram illustrating an example of a hardware configuration of a display terminal.

Next, a hardware configuration of the display terminal 3 will be described below with reference to FIG. 9. FIG. 9 is a diagram illustrating an example of the hardware configuration of the display terminal 3. As illustrated in FIG. 9, the display terminal 3 includes a controller 30, a storage device 31, a communication unit 32, an input operation unit 33, and a display 34. These components are communicably connected to one another via a bus 35. A type of the display terminal 3 is not particularly limited as long as the display terminal 3 is a display terminal managed by the medical worker and has a function (for example, a WEB browser) capable of displaying the patient information list screen (see FIG. 11 and the like) to be described later. The display terminal 3 may be a patient monitor, a personal computer, a workstation, a smartphone, a tablet, or a wearable device (for example, an AR glass or a head-mounted display) worn on a body (for example, an arm or a head) of a medical worker.

The controller 30 includes one or more memories and one or more processors. Each memory is configured to store a computer readable instruction (program). For example, the memory includes a ROM and a RAM. Each processor includes at least one of a CPU, an MPU, and a GPU, for example. The processor may be configured to load a program designated from various programs incorporated in the storage device 31 or ROM into RAM, and configured to execute various processes in cooperation with the RAM. The storage device 31 is a storage device such as an HDD, an SSD, or a flash memory, and is configured to store programs and various data.

The communication unit 32 is configured to connect the display terminal 3 to the communication network 5. Specifically, the communication unit 32 may include various wired connection terminals for communicating with each device disposed on the communication network 5. In addition, the communication unit 32 may include a wireless communication module for wirelessly communicating with each device. The input operation unit 33 is, for example, a touch panel, a mouse, and/or a keyboard, which are overlaid and disposed over the display 34. For example, in response to an input operation performed by the medical worker AA on the input operation unit 33, an input operation signal indicating the input operation performed by the medical worker AA is transmitted from the input operation unit 33 to the controller 30. Thereafter, the controller 30 executes a predetermined process in response to the received input operation signal. The display 34 includes, for example, a liquid crystal panel or an organic EL panel. The patient information list screen (see FIG. 11) to be described later is displayed on a display screen of the display 34. When the display terminal 3 is a head-mounted display, the patient information list screen may be disposed in a virtual space (Metaverse).

First Embodiment

Figure 10:
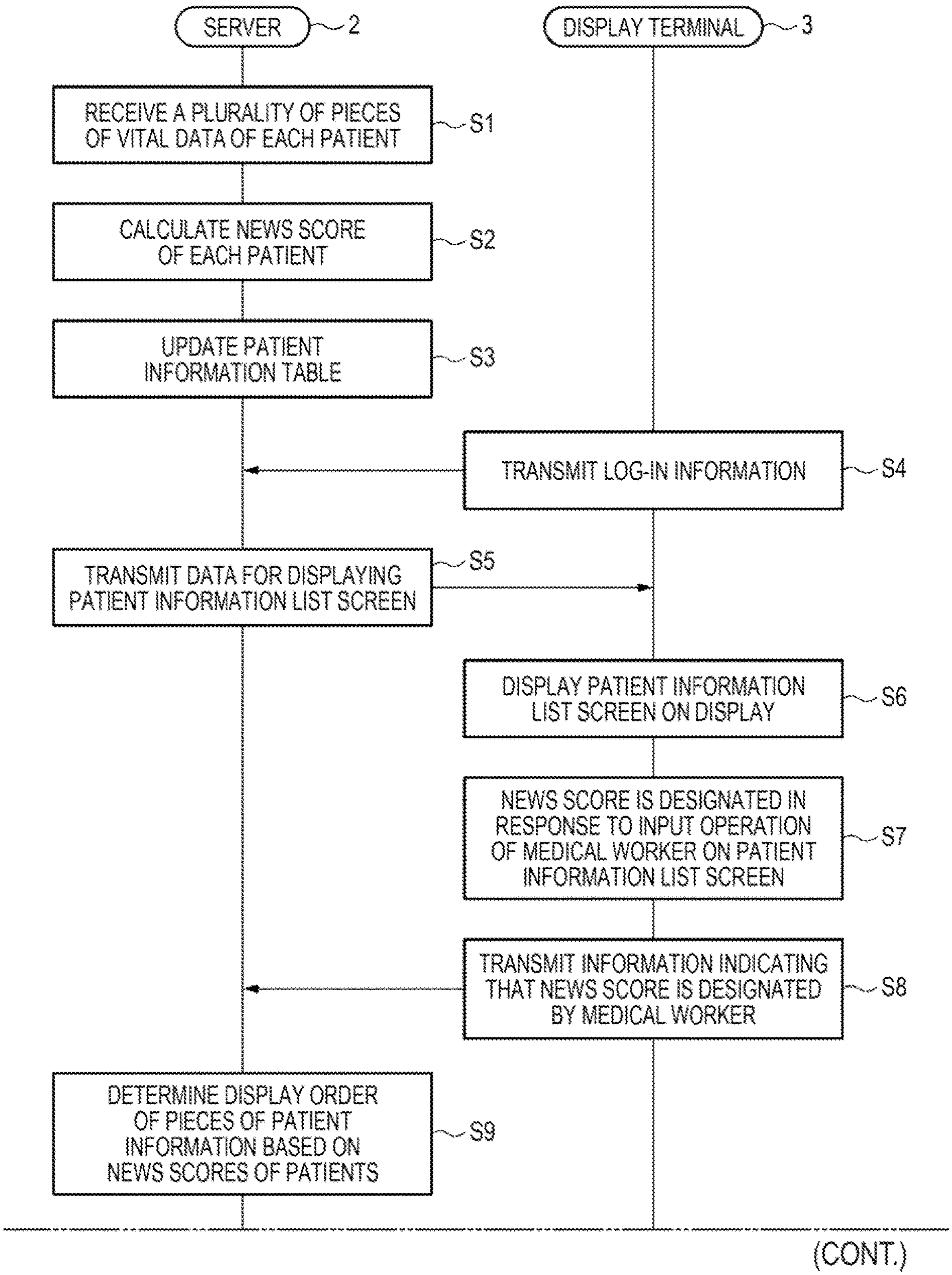
FIG. 10 is a sequence diagram illustrating a patient information processing method according to a first embodiment of the present disclosure.

Next, a patient information processing method according to a first embodiment of the present disclosure will be described below with reference to FIG. 10. FIG. 10 is a sequence diagram illustrating the patient information processing method according to the first embodiment. As illustrated in FIG. 10, the patient information processing method according to the first embodiment is executed by cooperation between the server 2 and the display terminal 3. In addition, in the following description, it is assumed that the medical worker AA accesses the server 2 through the display terminal 3.

In step S1, the server 2 obtains a plurality of pieces of vital data (respiration rate, oxygen saturation, body temperature, systolic blood pressure, and heart rate) of each of the patients A to Z from the plurality of bed-side monitors 6 connected to the patients A to Z. As described above, the server 2 may obtain the vital data of the patients A to Z from the bed-side monitors 6 via the communication network 5 at predetermined time intervals (for example, every day).

In step S2, the server 2 calculates a NEWS score of each of the patients A to Z based on the plurality of pieces of vital data of each of the patients A to Z, presence or absence of oxygen administration of each of the patients A to Z, and presence or absence of consciousness of each of the patients A to Z. As described above, the server 2 can calculate the NEWS score of the patient by summing a sub score of each piece of vital data, a sub score related to the oxygen administration, and a sub score related to the presence or absence of the consciousness.

In step S3, the server 2 updates the patient information table 41 illustrated in FIG. 4. In particular, the server 2 updates the information indicating the vital data of each patient, the information indicating the NEWS score of the patient, the information indicating the medical device connected to the patient, the information indicating the number of days in a hospital of the patient, the information indicating the presence or absence of the oxygen administration, and the information indicating the presence or absence of the consciousness of the patient.

Next, in step S4, the display terminal 3 transmits log-in information for accessing the server 2 to the server 2 via the communication network 5. Specifically, the display terminal 3 transmits the log-in information indicating a log-in ID and a password of the medical worker AA to the server 2.

In step S5, after authenticating the log-in information of the medical worker AA, the server 2 transmits, to the display terminal 3, data for displaying the patient information list screen on which a plurality of pieces of patient information are displayed. Here, the data for displaying the patient information list screen may be a code (HTML, CSS, Javascript, JSON data (or XML data), or the like) for displaying the patient information list screen on the WEB browser of the display terminal 3, or may be image data indicating the patient information list screen.

In step S6, the display terminal 3 displays the patient information list screen on the display screen of the display 34 based on the data for displaying the patient information list screen, which is received from the server 2. For example, the WEB browser installed in the display terminal 3 may render the patient information list screen by interpreting the data (HTML, CSS, JavaScript, JSON data (or XML data), or the like) for displaying the patient information list screen.

FIG. 11 illustrates an initial screen of the patient information list screen for the medical worker AA. In the patient information list screen illustrated in FIG. 11, the patient information of each of the patients A to Z includes the attribute information (patient name, bed location, age, gender, and the like) of the patient, the information indicating the vital data (respiration rate, SpO2, body temperature, systolic blood pressure, and heart rate) of the patient, and the information indicating the NEWS score. Further, since the patient information of the patients J, C, and W is pinned, the patient information of the patients J, C, and W is displayed at a head of the patient information list screen. In this regard, when the server 2 receives the log-in information indicating the medical worker AA, the server 2 specifies the patients J, C, and W that are pinned by the medical worker AA by referring to the pinning operation history table 43 (see FIG. 7). As described above, the data for displaying the patient information list screen transmitted to the display terminal 3 includes information indicating that the patients J, C, and W are pinned. A display order of the patient information of the pinned patients J, C, and W is not particularly limited.

Returning to FIG. 10, in step S7, the NEWS score (an example of the first information) is designated as a first priority parameter of the display order of the patient information in response to the input operation of the medical worker AA on the patient information list screen displayed on the display terminal 3. In this regard, by designating an item region L1 of the NEWS score on the patient information list screen through a click operation, the NEWS score may be designated as the first priority parameter for determining the display order of the patient information. Thereafter, the display terminal 3 transmits information indicating that the NEWS score is designated as the first priority parameter to the server 2 (step S8).

In step S9, when receiving the information indicating that the NEWS score is designated as the first priority parameter for determining the display order of the patient information, the server 2 determines a display order of the pieces of patient information based on the NEWS scores of the patients. In this regard, by referring to the patient information table 41 (see FIG. 4), the server 2 determines the display order of the pieces of patient information based on the NEWS scores such that the pieces of patient information to be displayed on the patient information list screen are displayed early according to values of the NEWS scores of the patients (that is, the pieces of patient information are arranged in a descending order according to the values of the NEWS scores).

Next, in step S10, the server 2 automatically designates the number of pinning operations (an example of second information) associated with each piece of patient information as a second priority parameter for determining the display order of the patient information. Here, the server 2 specifies the number of pinning operations associated with each piece of patient information by referring to the pinning operation history table 43 illustrated in FIG. 7. For example, as illustrated in FIG. 7, since the patient information of the patient C is pinned by the medical workers AA and DD, the number of pinning operations associated with the patient information of the patient C is two. Since the patient information of the patient Lis pinned only by a medical worker GG, the number of pinning operations associated with the patient information of the patient L is one.

Thereafter, the server 2 determines the display order of the patient information of patients having the same value of the NEWS score based on the number of pinning operations associated with each piece of patient information. For example, as illustrated in FIG. 12, when there are a plurality of patients having the same value of the NEWS score, the display order of the patients having the same value of the NEWS score is determined by the number of pinning operations different from the NEWS score. In the example illustrated in FIG. 12, since the number of pinning operations for the patients L, Q, U, Z, and Y whose NEWS scores are 5 is 1 (see FIG. 7), the patient information of the patients L, Q, U, Z, and Y is displayed earlier than the patient information of the patients B and V for whom the number of pinning operations is 0 (see a region R1 in FIG. 12).

In this example, since the patients J, C, and W are pinned by the medical worker AA, the display order of the pieces of patient information is determined such that the display order of the patient information of the patients J, C, and W is earlier than the display order of patient information of patients other than the patients J, C, and W. That is, the server 2 determines the display order of the patient information of the patients other than the patients J, C, and W pinned by the medical worker AA based on the two parameters, that is, the NEWS score and the number of pinning operations. For example, when there is no patient pinned by the medical worker AA, a display order of all the patient information is determined by the two parameters, that is, the NEWS score and the number of pinning operations.

Next, in step S11, the server 2 transmits, to the display terminal 3, the data for displaying the patient information list screen (see FIG. 12) on which the plurality of pieces of patient information are displayed in the determined display order. As described above, the data for displaying the patient information list screen may be a code for displaying the patient information list screen on the WEB browser of the display terminal 3, or may be image data indicating the patient information list screen.

In step S12, the display terminal 3 displays the patient information list screen on the display screen of the display 34 based on the data for displaying the patient information list screen, which is received from the server 2. Thus, as illustrated in FIG. 12, the pieces of patient information are displayed on the patient information list screen in a descending order based on the two parameters, that is, the NEWS score and the number of pinning operations.

When the pieces of patient information are displayed on the patient information list screen in an order according to a specific index such as a NEWS score, there is room for consideration in how to determine a display order of the patient information of patients having the same index. In contrast, according to the patient information processing method of the first embodiment, the display order of the pieces of patient information is determined based on the NEWS scores of the patients such that the pieces of patient information to be displayed on the patient information list screen are displayed early according to the values of the NEWS scores of the patients, and the display order of the pieces of patient information of the patients having the same NEWS score is determined based on the number of pinning operations. In this manner, the display order of the pieces of patient information to be displayed on the patient information list screen is finely determined based on the NEWS score and the number of pinning operations which are indexes different from each other. In this regard, the NEWS score indicates the condition of the patient, while the number of pinning operations indicates a degree of interest of the medical worker with respect to the patient. In this manner, the medical worker can easily grasp the patient information of the patient having a high priority through the patient information list screen displayed on the display terminal 3.

Since the NEWS score as the first priority parameter is determined according to the input operation of the medical worker who is a user, it is possible to customize the display order of the pieces of patient information to be displayed on the patient information list screen according to the input operation of the medical worker. Further, since the number of pinning operations, which is the second priority parameter, is automatically determined by the server 2 without any input operation of the medical worker, it is possible to save the labor of the input operation of the medical worker.

An order of processes illustrated in FIG. 10 is an example, and the order of the processes is not particularly limited. In particular, the processes of steps S9 to S11 (process of determining the display order of the patient information) may be executed by the display terminal 3 instead of the server 2. In this case, the patient information table 41 and the pinning operation history table 43 stored in the server 2 may be transmitted to the display terminal 3 before each process of steps S9 to S11 is executed by the display terminal 3. Although the patient information list screen is displayed on the display terminal 3 in the present embodiment, the patient information list screen may be displayed on the display 24 of the server 2. In this case, the medical worker AA operates the server 2 instead of the display terminal 3, whereby the patient information list screen is displayed on the display 24 of the server 2.

In this example, the display order of the patient information of the patients having the same NEWS score is determined based on the number of pinning operations, but the display order of the patient information of the patients having the same NEWS score may be determined according to the number of pinning operations and an attribute of the medical worker who is the user. For example, a predetermined weighting factor is determined according to a job type or years of experience of the medical worker, and then the display order of the patient information of the patients having the same NEWS score may be determined by a value obtained by multiplying the weighting factor by the number of pinning operations.

In the present embodiment, the display order of the pieces of patient information is determined based on the two parameters, that is, the NEWS score and the number of pinning operations, but parameters for determining the display order of the pieces of patient information is not limited to the NEWS score and the number of pinning operations. Hereinafter, a modification of the parameters for determining the display order of the pieces of patient information will be described.

(First Modification)

In a first modification of parameters for determining a display order of patient information, the NEWS score (an example of first information) may be adopted as a first priority parameter, and the number of characters (an example of second information) of the comment for the patient may be adopted as a second priority parameter. The number of characters of the comment for the patient is an example of information related to a predetermined operation of the medical worker for each patient information displayed on the patient information list screen, like the number of pinning operations.

In this case, in step S9 of FIG. 10, the server 2 determines the display order of the pieces of patient information based on the NEWS score by referring to the patient information table 41. Next, in step S10, the server 2 automatically designates the number of characters of the comment associated with each patient information as the second priority parameter for determining the display order of the patient information. Here, the server 2 specifies the number of characters of the comment associated with each patient information by referring to the patient comment table 44 illustrated in FIG. 8. For example, as illustrated in FIG. 8, the number of characters of a comment for the patient C made by the medical worker AA is 150, whereas the number of characters of the comment for the patient C made by the medical worker DD is 80. In this case, the number of characters of the comment associated with the patient information of the patient C is 230 (=150+80). Further, since the number of characters for the patient L commented by the medical worker GG is 120, the number of characters of a comment associated with the patient information of the patient Lis 120.

Thereafter, the server 2 determines a display order of patient information of patients having the same value of the NEWS score based on the number of characters of a comment associated with each piece of patient information. For example, as illustrated in FIG. 13, when there are a plurality of patients having the same value of the NEWS score, the display order of the patients having the same value of the NEWS score is determined by the number of characters of the comment different from the NEWS score. In the example illustrated in FIG. 13, the numbers of characters of the comments for the patients L, Q, and U whose NEWS scores are 5 are 120, 110, and 60, respectively (see FIG. 8). Therefore, the pieces of patient information of the patients L, Q, and U are displayed earlier than the pieces of patient information of the patients B, Y, V, and Z to which no comment is made (in other words, the numbers of characters of the comments are 0) (see a region R2 in FIG. 13). Further, the display order of the pieces of patient information of the patients L, Q, and U is displayed in descending order according to the numbers of characters of the comments for the patients L, Q, and U.

According to a patient information processing method of the first modification, the display order of the pieces of patient information is determined based on the NEWS score of each patient such that the pieces of patient information to be displayed on the patient information list screen are displayed early according to the values of the NEWS scores of the patients, and the display order of the pieces of patient information of the patients having the same value of the NEWS score is determined based on the number of characters of the comment for each patient (an example of information related to the comment for each patient). In this manner, the display order of the pieces of patient information to be displayed on the patient information list screen is finely determined based on the NEWS score and the number of characters of the comment for each patient, which are indexes different from each other. In this regard, the NEWS score indicates the condition of the patient, while the number of characters of the comment indicates a degree of interest of the medical worker with respect to the patient. In this manner, the medical worker can easily grasp the patient information of the patient having a high priority through the patient information list screen displayed on the display terminal 3.

In the first modification, the display order of the pieces of patient information of the patients having the same NEWS score is determined based on the number of characters of the comment for each patient as an example of the information related to the comment for each patient, but this example is not limited to this. In this regard, the display order of the pieces of patient information of the patients having the same NEWS score may be determined in accordance with the number of inputs of the comment to each patient, a total number of inputs of the comment to each patient within a predetermined period (more specifically, a period from the time of logging to a pre-predetermined-time), or the number of inputs of the comment for each patient within the predetermined period.

(Second Modification)

In a second modification of parameters for determining a display order of patient information, the NEWS score (an example of first information) may be adopted as a first priority parameter, and the number of days in a hospital (an example of second information) of the patient may be adopted as a second priority parameter.

In this case, in step S9 of FIG. 10, the server 2 determines the display order of the pieces of patient information based on the NEWS score by referring to the patient information table 41. Next, in step S10, the server 2 automatically designates the number of days in a hospital of each patient as the second priority parameter for determining the display order of the patient information. Here, the server 2 specifies the number of days in a hospital of each patient by referring to the patient information table 41 illustrated in FIG. 4.

Thereafter, the server 2 determines the display order of the patient information of the patients having the same value of the NEWS score based on the number of days in a hospital of each patient. For example, as illustrated in FIG. 14, when there are a plurality of patients having the same value of the NEWS score, the display order of the patients having the same value of the NEWS score is determined by the number of days in a hospital of the patient different from the NEWS score. In the example illustrated in FIG. 14, the numbers of days in a hospital of the patients N, I, and X whose NEWS scores are 9 are 32, 4, and 2, respectively (see FIG. 4). Therefore, patient information of the patients N, I, and X is displayed in the order of N, I, and X according to the numbers of days in a hospital of the patients. The patient information of the patients having the same value of the NEWS score is displayed in descending order according to the number of days in a hospital of the patient.

According to a patient information processing method of the second modification, the display order of the pieces of patient information is determined based on the NEWS scores of the patients such that the pieces of patient information to be displayed on the patient information list screen are displayed early according to the values of the NEWS scores of the patients, and the display order of the pieces of patient information of the patients having the same NEWS score is determined based on the number of days in a hospital of each patient. In this manner, the display order of the pieces of patient information to be displayed on the patient information list screen is finely determined based on the NEWS score and the number of days in a hospital of each patient which are indexes different from each other. In this regard, the NEWS score indicates the condition of the patient, while the number of days in a hospital of the patient indicates a degree of intervention in the patient performed by a medical institution. In this manner, the medical worker can easily grasp the patient information of the patient having a high priority through the patient information list screen displayed on the display terminal 3.

(Third Modification)

In a third modification of parameters for determining a display order of patient information, the NEWS score (an example of first information) may be adopted as a first priority parameter, information (an example of second information) indicating whether a specific medical device is connected to each patient may be adopted as a second priority parameter. In this example, ECMO and a respirator connected to a severe patient infected with a novel coronavirus are specific medical devices. The specific medical device is not limited to ECMO or the respirator, and may be a pacemaker or the like.

In this case, in step S9 of FIG. 10, the server 2 determines the display order of the pieces of patient information based on the NEWS score by referring to the patient information table 41. Next, in step S10, the server 2 automatically designates information indicating whether ECMO or the respirator is connected to each patient as the second priority parameter for determining the display order of the patient information. Here, the server 2 specifies whether ECMO or the respirator is connected to each patient by referring to the patient information table 41 illustrated in FIG. 4.

Thereafter, the server 2 determines a display order of patient information of patients having the same value of the NEWS score based on whether ECMO or the respirator is connected. For example, as illustrated in FIG. 15, when there are a plurality of patients having the same value of the NEWS score, the display order of the patients having the same value of the NEWS score is determined depending on whether ECMO or the respirator is connected. In the example illustrated in FIG. 15, only the patients E and R are connected to ECMO among patients whose NEWS scores are 6. Therefore, among patient information of the patients whose NEWS scores are 6, patient information of the patients E and R is preferentially displayed first. Among patients whose NEWS scores are 5, the patient Y is connected to ECMO, and the patient Q is connected to the respirator. Therefore, among patient information of the patients whose NEWS scores are 5, patient information of the patients Y and Q is preferentially displayed first. In this regard, since a patient connected to ECMO is given priority over a patient connected to the respirator, the patient information of the patient Y is displayed prior to the patient information of the patient Q. In this way, in this example, a priority order of patient information to be displayed on the patient information list screen may be determined depending on a type of the medical device connected to the patient.

According to a patient information processing method of the third modification, the display order of the pieces of patient information is determined based on the NEWS scores of the patients such that the pieces of patient information to be displayed on the patient information list screen are displayed early according to the values of the NEWS scores of the patients, and the display order of the pieces of patient information of the patients having the same NEWS score is determined based on whether ECMO or the respirator is connected. In this manner, the display order of the pieces of patient information to be displayed on the patient information list screen is finely determined based on the NEWS score and the presence or absence of the connection of ECMO or the respirator, which are indexes different from each other. In this regard, the NEWS score indicates the condition of the patient, and the presence or absence of the connection of ECMO or the respirator indicates severity of a respirator function of the patient. In this manner, the medical worker can easily grasp the patient information of the patient having a high priority through the patient information list screen displayed on the display terminal 3.

(Fourth Modification)

In a fourth modification of parameters for determining a display order of patient information, the NEWS score (an example of first information) is adopted as a first priority parameter, information (an example of second information) indicating whether a specific medical device (for example, ECMO or a respirator) is connected to each patient is adopted as a second priority parameter, and the number of days in a hospital (an example of third information) of each patient is adopted as a third priority parameter. As described above, the specific medical device is not limited to ECMO or the respirator.

In this case, in step S9 of FIG. 10, the server 2 determines the display order of the pieces of patient information based on the NEWS score by referring to the patient information table 41. Next, in step S10, the server 2 automatically designates information indicating whether ECMO or the respirator is connected to each patient as the second priority parameter for determining the display order of the patient information. Here, the server 2 specifies whether ECMO or the respirator is connected to each patient by referring to the patient information table 41 illustrated in FIG. 4. Further, the server 2 automatically designates the number of days in a hospital of each patient as the third priority parameter for determining the display order of the patient information. Here, the server 2 specifies the number of days in a hospital of each patient by referring to the patient information table 41 illustrated in FIG. 4.

Thereafter, the server 2 determines a display order of patient information of patients having the same value of the NEWS score based on whether ECMO or the respirator is connected. For example, as illustrated in FIG. 16, when there are a plurality of patients having the same value of the NEWS score, the display order of the patients having the same value of the NEWS score is determined depending on whether ECMO or the respirator is connected. In the example illustrated in FIG. 16, only the patients E and R are connected to ECMO among patients whose NEWS scores are 6. Therefore, among patient information of the patients whose NEWS scores are 6, patient information of the patients E and R is preferentially displayed first.

Further, the server 2 determines the display order of the patient information of the patients (specifically, the patients P, K, T, and F) having the NEWS score of 6 excluding the patients E and R connected to ECMO, based on the number of days in a hospital of each patient. In the example illustrated in FIG. 16, the numbers of days in a hospital of the patients P, K, T, and F whose NEWS scores are 9 are 84 days, 68 days, 6 days, and 3 days, respectively (see FIG. 4). Therefore, the patient information of the patients P, K, T, and F is displayed in the order of P, K, T, and F according to the number of days in a hospital of each patient. In this way, the display order of the pieces of patient information is determined according to a priority order of the value of the NEWS score (first priority)→the presence or absence of the connection of ECMO or the respirator (second priority)→the number of days in a hospital of each patient (third priority).

According to a patient information processing method of the fourth modification, the display order of the pieces of patient information is determined based on the NEWS scores of the patients such that the pieces of patient information to be displayed on the patient information list screen are displayed early according to the values of the NEWS scores of the patients, and the display order of the pieces of patient information of the patients having the same NEWS score is determined based on whether ECMO or the respirator is connected. Further, based on the number of days in a hospital of each patient, the display order of the pieces of the patient information of the patients having the same NEWS score, excluding the patients connected to ECMO or the respirator, is determined.

In this manner, the display order of the pieces of patient information to be displayed on the patient information list screen is finely determined based on the NEWS score, the presence or absence of the connection of ECMO or the respirator, and the number of days in a hospital, which are indexes different from one another. In this regard, the NEWS score indicates the condition of the patient, and the presence or absence of the connection of ECMO or the respirator indicates severity of a respirator function of the patient. The number of days in a hospital of each patient indicates a degree of intervention in the patient performed by a medical institution. In this manner, the medical worker can easily grasp the patient information of the patient having a high priority through the patient information list screen displayed on the display terminal 3.

Information indicating an attribute of the patient or the medical worker may be used as priority parameters for determining the display order of the pieces of patient information. In this regard, the server 2 may determine the display order of the patient information of the patients having the same value of the NEWS score based on the information indicating the attribute of the patient or the medical worker. The information indicating the attribute of the patient may be an age of the patient or a floor of a bed location of the patient. Further, the information indicating the attribute of the medical worker may be a department to which the medical worker belongs. For example, when a department of the medical worker AA who accesses the server 2 through the display terminal 3 is a cardiovascular medicine, the server 2 may preferentially display patient information related to the cardiovascular medicine among the patient information of the patients having the same value of the NEWS score.

In the present embodiment and the modifications, although the NEWS score is used as the first priority parameter, the first priority parameter may be another index (for example, the number of days in a hospital of the patient) other than the NEWS score.

Second Embodiment

Figure 17:
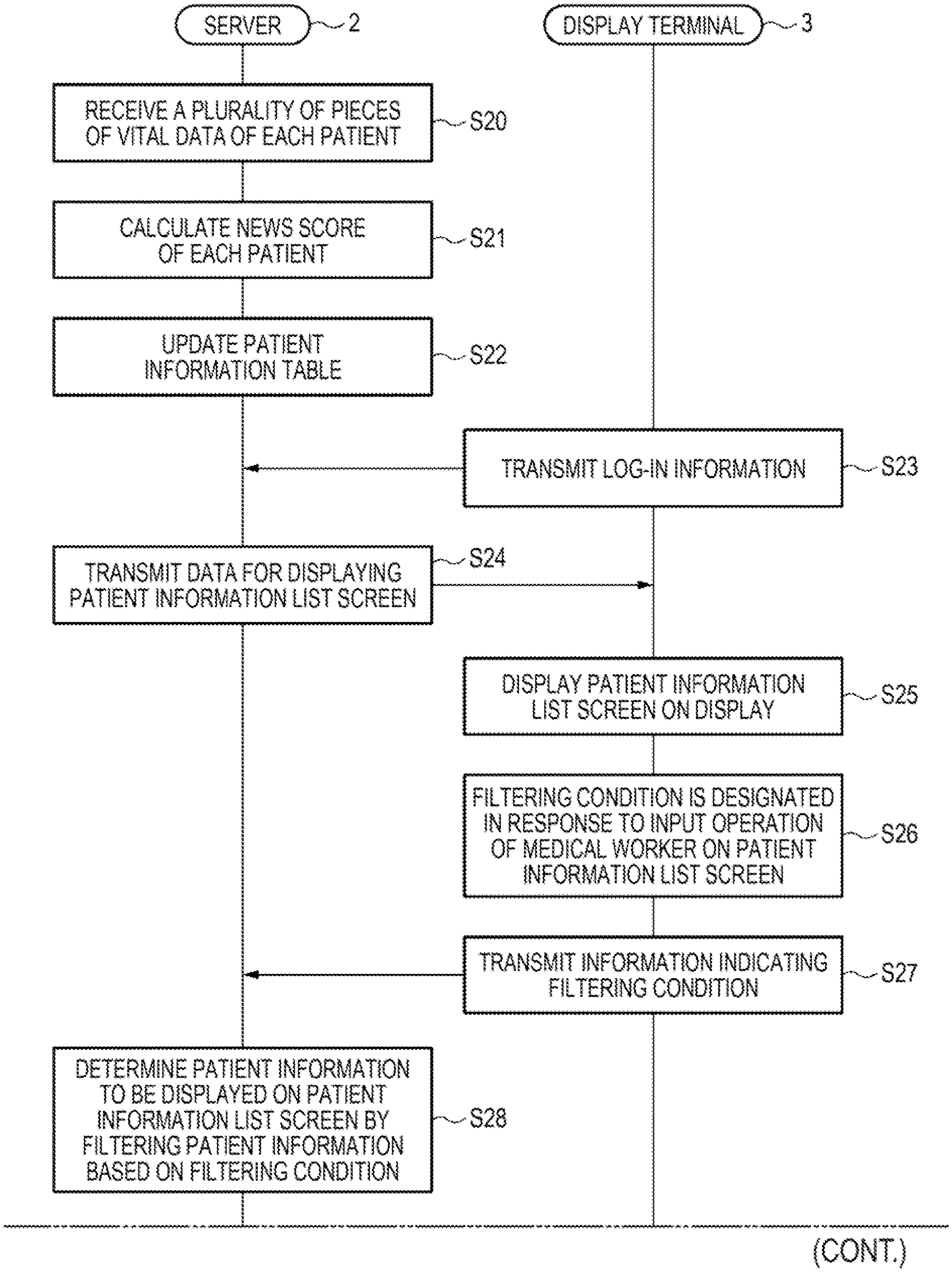
FIG. 17 is a sequence diagram illustrating a patient information processing method according to a second embodiment of the present disclosure.

Next, a patient information processing method according to a second embodiment of the present disclosure will be described below, mainly with reference to FIGS. 17 and 18. FIG. 17 is a sequence diagram illustrating the patient information processing method according to the second embodiment. FIG. 18 is a diagram illustrating an example of a patient information list screen in which a display order of patient information satisfying a filtering condition in which a bed location of a patient is 3F is determined according to an NEWS score. As illustrated in FIG. 17, it is assumed that the patient information processing method according to the second embodiment is executed by cooperation between the server 2 and the display terminal 3, and the medical worker AA accesses the server 2 through the display terminal 3.

In step S20, the server 2 obtains a plurality of pieces of vital data of each of the patients A to Z from the plurality of bed-side monitors 6. In step S21, the server 2 calculates a NEWS score of each of the patients A to Z based on the plurality of pieces of vital data of each of the patients A to Z, presence or absence of oxygen administration of each of the patients A to Z, and presence or absence of consciousness of each of the patients A to Z. In step S22, the server 2 updates the patient information table 41 illustrated in FIG. 4.

Next, in step S23, the display terminal 3 transmits log-in information (for example, a log-in ID and a password) for accessing the server 2 to the server 2 via the communication network 5. In step S24, after authenticating the log-in information of the medical worker AA, the server 2 transmits, to the display terminal 3, data for displaying the patient information list screen on which a plurality of pieces of patient information are displayed.

In step S25, the display terminal 3 displays the patient information list screen on the display screen of the display 34 based on the data for displaying the patient information list screen, which is received from the server 2. In this regard, a WEB browser installed in the display terminal 3 may render the patient information list screen by interpreting the data for displaying the patient information list screen.

In step S26, the filtering condition for filtering the patient information is designated in response to the input operation of the medical worker AA on the patient information list screen displayed on the display terminal 3. In this example, it is assumed that the filtering condition in which the bed location (location floor) of the patient is 3F is input by the medical worker AA. An input region for designating the filtering condition may be provided in the patient information list screen. Thereafter, the display terminal 3 transmits information indicating the filtering condition in which the bed location of the patient is 3F to the server 2 (step S27).

In step S28, after receiving the information indicating the filtering condition, the server 2 determines the patient information to be displayed on the patient information list screen by filtering the patient information based on the filtering condition. In this regard, the server 2 extracts the patient information of the patient whose bed location is 3F by referring to the patient information table 41 (see FIG. 4). In this filtering process, even if the patient is pinned by the medical worker AA, when the bed location of the patient is not 3F, the patient information of the patient is not extracted as the patient information to be displayed on the patient information list screen.

Next, in step S29, the server 2 determines the display order of the patient information satisfying the filtering condition (in other words, the patient information extracted based on the filtering condition) according to the NEWS score of each patient. In this regard, by referring to the patient information table 41 (see FIG. 4), the server 2 determines the display order of the pieces of patient information based on the NEWS scores such that the pieces of patient information to be displayed on the patient information list screen are displayed early according to values of the NEWS scores of the patients (that is, the pieces of patient information are arranged in a descending order according to the values of the NEWS scores).

Next, in step S30, the server 2 transmits, to the display terminal 3, the data for displaying the patient information list screen (see FIG. 18) on which the plurality of pieces of patient information are displayed in the determined display order. As described above, the data for displaying the patient information list screen may be a code for displaying the patient information list screen on the WEB browser of the display terminal 3, or may be image data indicating the patient information list screen.

In step S31, the display terminal 3 displays the patient information list screen on the display screen of the display 34 based on the data for displaying the patient information list screen, which is received from the server 2. Thus, as illustrated in FIG. 18, the pieces of patient information are displayed on the patient information list screen in the descending order based on the NEWS score.

According to the patient information processing method of the second embodiment, the plurality of pieces of patient information (in this example, the patient information of the patient whose bed location is 3F) displayed on the patient information list screen are determined by filtering the plurality of pieces of patient information based on the filtering condition, and the display order of the pieces of patient information to be displayed on the patient information list screen is determined based on information (in this example, the NEWS score) different from the filtering condition. As described above, since the patient information to be displayed on the patient information list screen and the display order of the patient information are determined based on the two different information, that is, the filtering condition and the NEWS score, the medical worker can easily grasp the patient information having a high priority through the patient information list screen.

In the description of the present embodiment, a condition related to the attribute of the patient (specifically, the location floor of the patient) is designated as the filtering condition by the medical worker AA, but the filtering condition is not particularly limited. In this regard, the condition related to the attribute of the medical worker (user) may be input as the filtering condition, or the condition related to the vital data or the NEWS score of the patient may be designated as the filtering condition. For example, as the filtering condition, patient information in which the NEWS score is greater than or equal to a predetermined value may be extracted. Further, patient information in which the number of days in a hospital is a predetermined number of days or more may be extracted.

In the present embodiment, the display order of the extracted patient information is determined according to the NEWS score, but the parameter for determining the display order of the patient information is not limited to the NEWS score. For example, the display order of the patient information may be determined based on the number of days in a hospital of the patient or the presence or absence of the medical device connected to the patient, or the display order of the patient information may be determined based on a plurality of priority parameters (for example, a NEWS score and the number of characters of a comment).

(Modification of Second Embodiment)

Figure 19:
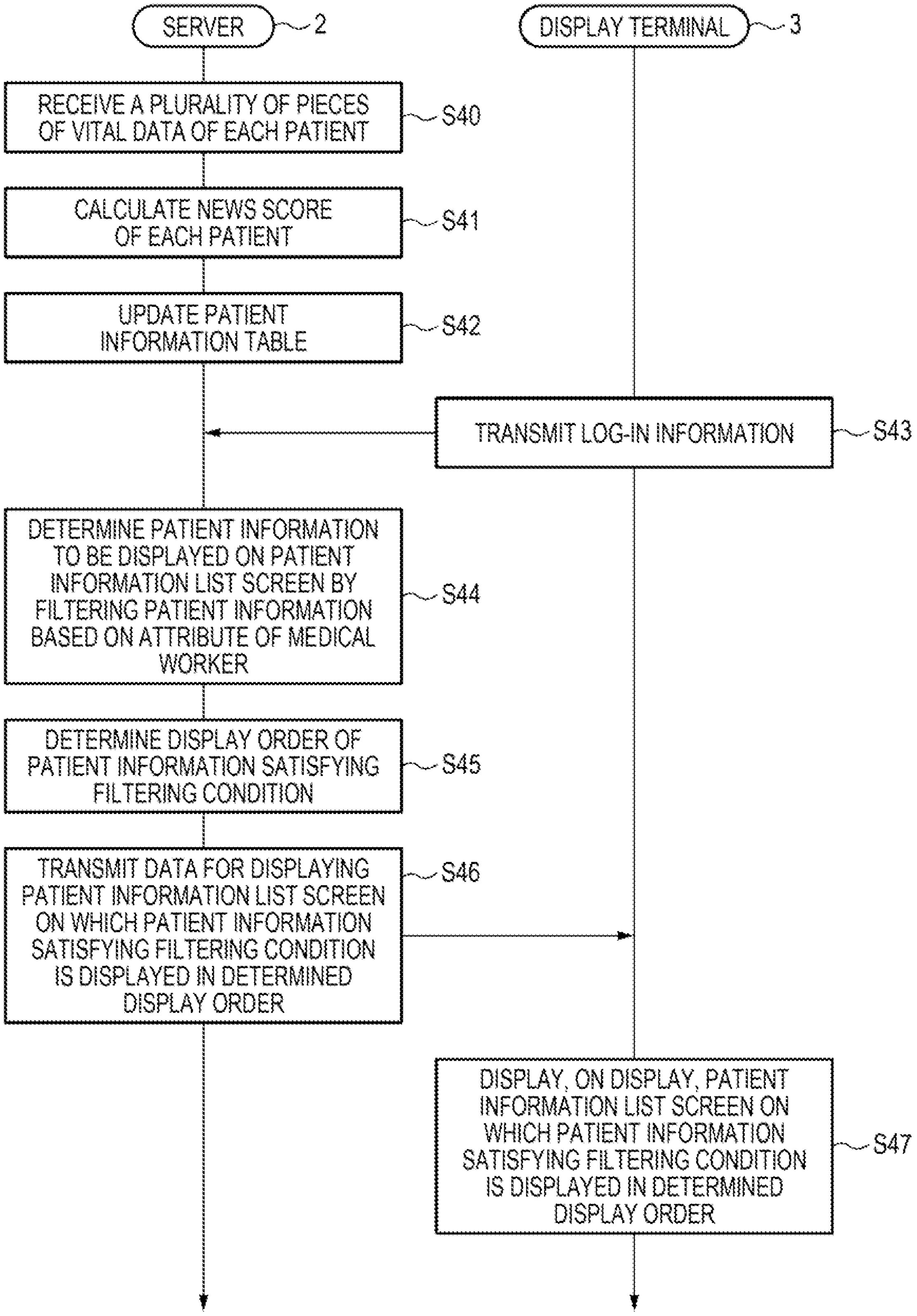
FIG. 19 is a sequence diagram illustrating a patient information processing method according to a modification of the second embodiment.

Next, a patient information processing method according to a modification of the second embodiment will be described below with reference to FIG. 19. FIG. 19 is a sequence diagram illustrating the patient information processing method according to the modification of the second embodiment. The present modification is different from the patient information processing method according to the second embodiment in that the filtering condition is automatically determined on a server 2 side based on the attribute of the medical worker who accesses the server 2. In this modification, it is also assumed that the medical worker AA accesses the server 2 through the display terminal 3.

As illustrated in FIG. 19, in step S40, the server 2 obtains a plurality of pieces of vital data of each of the patients A to Z from the plurality of bed-side monitors 6. In step S41, the server 2 calculates the NEWS scores of the patients A to Z. In step S42, the server 2 updates the patient information table 41 illustrated in FIG. 4.

Next, in step S43, the display terminal 3 transmits log-in information (for example, a log-in ID and a password) for accessing the server 2 to the server 2 via the communication network 5. In step S44, after authenticating the log-in information of the medical worker AA, the server 2 automatically determines the patient information to be displayed on the patient information list screen by filtering the patient information based on the attribute of the medical worker AA. In this regard, the server 2 specifies the attribute of the medical worker AA by referring to the medical worker information table illustrated in FIG. 6. Thereafter, the server 2 filters the patient information based on the attribute of the medical worker AA by referring to the patient information table 41 illustrated in FIG. 4. For example, the server 2 may specify a cardiovascular medicine to which the medical worker AA belongs and then extract the patient information of the patient present on the same floor as the floor on which the cardiovascular medicine is provided.

Next, in step S45, the server 2 determines the display order of the patient information satisfying the filtering condition according to the NEWS score of each patient. In step S46, the server 2 transmits, to the display terminal 3, the data for displaying the patient information list screen on which the plurality of pieces of patient information are displayed in the determined display order. In step S47, the display terminal 3 displays the patient information list screen on the display screen of the display 34 based on the data for displaying the patient information list screen, which is received from the server 2. In this manner, the patient information is automatically extracted according to the attribute of the medical worker, and the display order of the extracted patient information is automatically determined according to the NEWS score.

According to the patient information processing method of the modification of the second embodiment, the plurality of pieces of patient information to be displayed on the patient information list screen are automatically determined by filtering the plurality of pieces of patient information based on the attribute of the medical worker (user), the display order of the pieces of patient information to be displayed on the patient information list screen is determined based on the NEWS score. In this way, since the patient information to be displayed on the patient information list screen and the display order of the patient information are automatically determined on the server side, the medical worker can easily grasp the patient information having a high priority through the patient information list screen. In particular, since the patient information to be displayed on the patient information list screen is automatically extracted and sorted without an input operation of the filtering condition performed by the medical worker, usability of the patient information processing system can be further improved.

In order to implement the patient information processing method according to the present embodiment by software, a patient information processing program may be incorporated in advance in a storage device and/or the ROM of the server 2 and/or the display terminal 3. Alternatively, the patient information processing program may be stored in a computer readable storage medium such as a magnetic disk (for example, HDD and a floppy disk), an optical disk (for example, CD-ROM, DVD-ROM, and Blu-ray (registered trademark) disk), a magneto optical disk (for example, MO), or a flash memory (for example, an SD card, a USB memory, and SSD). In this case, the patient information processing program stored in the storage medium may be incorporated in the storage device. Further, after the program incorporated in the storage device is loaded onto RAM, one or more processors may execute the program loaded on RAM. In this manner, the patient information processing method according to the present embodiment is executed by the server 2 and/or the display terminal 3. In addition, the patient information processing program may be downloaded from an external computer on a communication network. In this case, the downloaded program may be also incorporated in the storage device.

Although the embodiments of the presently disclosed subject matter have been described above, the technical scope of the presently disclosed subject matter should not be construed as being limited to the description of the present embodiments. The present embodiments are merely an example, and it is understood by those skilled in the art that various modifications of the embodiments are possible within the scope of the disclosed subject matters described in the claims. The technical scope of the presently disclosed subject matter should be determined based on the scope of the disclosed subject matters described in the claims and equivalents thereof.

What is claimed is:

1. A patient information processing method executed by one or more processors, the method comprising:

receiving a plurality of pieces of vital data of the plurality of patients;

calculating a vital score indicating a condition of the patient for each patient by using at least the plurality of pieces of vital data;

obtaining a plurality of pieces of patient information each of which is associated with respective one of a plurality of patients, each of the plurality of pieces of patient information including the plurality of vital data associated with a corresponding patient and information indicating the vital score;

determining a display order of the pieces of patient information to be displayed on a patient information list screen based on first information and second information different from the first information, the first information being the information indicating the vital score of each patient, and displaying the patient information list screen on which the plurality of pieces of patient information are displayed in the determined display order;

wherein the determining the display order includes determining the display order of the pieces of patient information based on the vital scores of the patients such that the pieces of patient information to be displayed on the patient information list screen are displayed early according to a value of the vital score of each patient, and determining a display order of patient information of patients having the same value of the vital score based on the second information.

2. The patient information processing method according to claim 1, wherein the first information is determined according to an input operation of a user on the patient information list screen.

3. The patient information processing method according to claim 2, wherein the second information is automatically determined without an input operation of a user on the patient information list screen.

4. The patient information processing method according to claim 1, wherein the second information is information related to a predetermined operation of the user for each piece of patient information displayed on the patient information list screen.

5. The patient information processing method according to claim 4, wherein the second information is information related to a comment for each piece of patient information, and the step of determining the display order includes a step of determining the display order of the patient information of the patients having the same value of the vital score based on the information related to the comment associated with each piece of patient information.

6. The patient information processing method according to claim 1, wherein the second information is information indicating whether a specific medical device is connected to each patient, and the step of determining the display order includes a step of determining the display order of the patient information of the patients having the same value of the vital score based on the information indicating whether the specific medical device is connected to each patient.

7. The patient information processing method according to claim 6, wherein the specific medical device is an extracorporeal membrane oxygenation (ECMO).

8. The patient information processing method according to claim 1, wherein the second information is information indicating the number of days in a hospital of each patient, and the step of determining the display order includes a step of determining the display order of the patient information of the patients having the same value of the vital score based on the number of days in a hospital of each patient.

9. The patient information processing method according to claim 1, wherein the second information is information related to an attribute of the user, and the step of determining the display order includes a step of determining the display order of the patient information of the patients having the same value of the vital score based on the attribute of the user.

10. The patient information processing method according to claim 1, wherein in the step of determining the display order, the display order of the pieces of patient information is determined such that predetermined patient information pinned by the user is displayed earlier than patient information other than the predetermined patient information, and a display order of the patient information other than the predetermined patient information is determined based on the vital score and the second information.

11. A patient information processing method executed by one or more processors, the method comprising:

receiving a plurality of pieces of vital data of the plurality of patients;

calculating a vital score indicating a condition of the patient for each patient by using at least the plurality of pieces of vital data;

obtaining a plurality of pieces of patient information each of which is associated with respective one of a plurality of patients, each of the plurality of pieces of patient information including the plurality of vital data associated with a corresponding patient and information indicating the vital score;

determining a plurality of pieces of first patient information to be displayed on a patient information list screen by filtering the plurality of pieces of patient information based on a predetermined filtering condition; and determining a display order of the plurality of pieces of first patient information to be displayed on the patient information list screen based on information different from the predetermined filtering condition, the information different from the predetermined filtering condition being the information indicating the vital score of each patient; and displaying the patient information list screen on which the plurality of pieces of patient information are displayed in the determined display order.

12. The patient information processing method according to claim 11, wherein the predetermined filtering condition is information related to an attribute of a user or the patient.

13. A non-transitory computer readable medium that stores a program that causes a computer to execute the patient information processing method according to claim 1.

14. A patient information processing device comprising:

one or more processors; and one or more memories configured to store a computer readable instruction, wherein when the computer readable instruction is executed by the one or more processors, the patient information processing device receives a plurality of pieces of vital data of the plurality of patients;

calculates a vital score indicating a condition of the patient for each patient by using at least the plurality of pieces of vital data;

obtains a plurality of pieces of patient information each of which is associated with respective one of a plurality of patients, each of the plurality of pieces of patient information including the plurality of vital data associated with a corresponding patient and information indicating the vital score;

determines a display order of the pieces of patient information to be displayed on a patient information list screen based on first information and second information different from the first information, the first information being the information indicating the vital score of each patient, and displays the patient information list screen on which the plurality of pieces of patient information are displayed in the determined display order;

when determining the display order, the patient information processing device determines the display order of the pieces of patient information based on the first information such that the pieces of patient information to be displayed on the patient information list screen are displayed early according to a value of the of the vital score, and determines a display order of patient information of patients having the same value of the vital score based on the second information.

15. A patient information processing device comprising:

one or more processors; and one or more memories configured to store a computer readable instruction, wherein when the computer readable instruction is executed by the one or more processors, the patient information processing device receives a plurality of pieces of vital data of the plurality of patients;

calculates a vital score indicating a condition of the patient for each patient by using at least the plurality of pieces of vital data;

obtains a plurality of pieces of patient information each of which is associated with respective one of a plurality of patients, each of the plurality of pieces of patient information including the plurality of vital data associated with a corresponding patient and information indicating the vital score;

determines a plurality of pieces of first patient information to be displayed on a patient information list screen by filtering the plurality of pieces of patient information based on a predetermined filtering condition, determines a display order of the plurality of pieces of first patient information to be displayed on the patient information list screen based on information different from the predetermined filtering condition, the information different from the predetermined filtering condition being the information indicating the vital score of each patient; and displays the patient information list screen on which the plurality of pieces of patient information are displayed in the determined display order.

16. A patient information processing system comprising:

a server; and a display terminal communicably connected to the server, wherein the patient information processing system receives a plurality of pieces of vital data of the plurality of patients;

calculates a vital score indicating a condition of the patient for each patient by using at least the plurality of pieces of vital data;

obtains a plurality of pieces of patient information each of which is associated with respective one of a plurality of patients, each of the plurality of pieces of patient information including the plurality of vital data associated with a corresponding patient and information indicating the vital score;

determines a display order of the pieces of patient information to be displayed on a patient information list screen based on first information and second information different from the first information, the first information being the information indicating the vital score of each patient, and displays the patient information list screen in which the plurality of pieces of patient information are displayed in the determined display order, and when determining the display order, the patient information processing system determines the display order of the pieces of patient information based on the vital score such that the pieces of patient information to be displayed on the patient information list screen are displayed early according to a value of the first information, and determines a display order of patient information of patients having the same value of the vital score based on the second information.

17. A patient information processing system comprising:

a server; and a display terminal communicably connected to the server, wherein the patient information processing system obtains a plurality of pieces of patient information each of which is associated with respective one of a plurality of patients, receives a plurality of pieces of vital data of the plurality of patients;

calculates a vital score indicating a condition of the patient for each patient by using at least the plurality of pieces of vital data;

determines a plurality of pieces of first patient information to be displayed on a patient information list screen by filtering the plurality of pieces of patient information based on a predetermined filtering condition, each of the plurality of pieces of first patient information including the plurality of vital data associated with a corresponding patient and information indicating the vital score;

determines a display order of the plurality of pieces of first patient information to be displayed on the patient information list screen based on information different from the predetermined filtering condition, and displays the patient information list screen on which the plurality of pieces of first patient information are displayed in the determined display order, the information different from the predetermined filtering condition being the information indicating the vital score of each patient.

* * * * *